(12) United States Patent
Worthington

(10) Patent No.: US 8,679,821 B2
(45) Date of Patent: Mar. 25, 2014

(54) BACTERIOPHAGE DERIVED METHODS TO CONTROL LACTIC ACID BACTERIAL GROWTH

(75) Inventor: Ronald E. Worthington, Edwardsville, IL (US)

(73) Assignee: Southern Illinois University Edwardsville, Edwardsville, IL (US)

( * ) Notice: Subject to any disclaimer, the term of this patent is extended or adjusted under 35 U.S.C. 154(b) by 271 days.

(21) Appl. No.: 13/130,544

(22) PCT Filed: Nov. 23, 2009

(86) PCT No.: PCT/US2009/065569
§ 371 (c)(1),
(2), (4) Date: Jul. 12, 2011

(87) PCT Pub. No.: WO2010/060054
PCT Pub. Date: May 27, 2010

(65) Prior Publication Data
US 2011/0262411 A1    Oct. 27, 2011

Related U.S. Application Data

(60) Provisional application No. 61/117,104, filed on Nov. 22, 2008.

(51) Int. Cl.
*C12N 1/20* (2006.01)
*C12P 21/06* (2006.01)
*C07H 21/02* (2006.01)

(52) U.S. Cl.
USPC ............ 435/252.3; 536/23.1; 435/69.1

(58) Field of Classification Search
USPC ............ 435/23.1, 69.1, 252.3; 536/23.1
See application file for complete search history.

(56) References Cited

U.S. PATENT DOCUMENTS

| | | | |
|---|---|---|---|
| 4,740,593 | A | 4/1988 | Gonzalez et al. |
| 5,722,342 | A | 3/1998 | Line et al. |
| 2006/0154338 | A1 | 7/2006 | Stahl |
| 2006/0216356 | A1 | 9/2006 | Mansfield et al. |
| 2007/0092956 | A1 | 4/2007 | Rajgarhia et al. |

FOREIGN PATENT DOCUMENTS

WO    WO2010060057 A1    5/2010

OTHER PUBLICATIONS

Sequence alignment between SEQ ID No. 5 and Accession No. AY968582 (2005).*
Greenspan et al (Nature Biotechnology 7: 936-937, 1999).
Chothia et al (The EMBO Journal, 1986,5/4:823-26).
Mikayama et al. (Nov. 1993. Proc.Natl.Acad.Sci. USA, vol. 90 : 10056-10060).
Rudinger et al. (Jun. 1976. Peptide Hormones. Biol.Council. pp. 5-7).
Office Action issued in U.S. Appl. No. 13/130,546 dated Mar. 26, 2013.
De Oliva Neto et al., Screening for yeast with antibacterial properties from an ethanol distillery, Bioresource Technology 2004, 92:1-6 (6 pages).
International Search Report and Written Opinion for International Publication No. WO2010/060054A1 (PCT/US2009/065569) dated Mar. 4, 2010 (10 pages).
International Search Report and Written Opinion for International Publication No. WO2010/060057A1 (PCT/US2009/065573) dated Mar. 17, 2010 (9 pages).

* cited by examiner

*Primary Examiner* — Tekchand Saidha
(74) *Attorney, Agent, or Firm* — Polsinelli PC

(57) ABSTRACT

Compositions and methods for protection against bacterial contamination are disclosed Antibacterial proteins and methods of use thereof are also disclosed.

21 Claims, 4 Drawing Sheets

US 8,679,821 B2

BACTERIOPHAGE DERIVED METHODS TO CONTROL LACTIC ACID BACTERIAL GROWTH

CROSS-REFERENCE TO RELATED APPLICATIONS

This application is a national stage application of PCT International Patent Application No. PCT/US2009/065569 filed Nov. 23, 2009 and also claims priority of U.S. Provisional Application Ser. No. 61/117,104 filed on Nov. 22, 2008, the subject matter of each above-mentioned applications are herein being incorporated by reference in their entirety.

FIELD OF INVENTION

The present invention relates to novel antibacterial proteins and nucleic acid sequences. Specifically, the invention includes antibacterial protein compositions, methods of use, and transgenic organisms encompassing the antibacterial proteins.

BACKGROUND OF INVENTION

Bacteria are everywhere—from our intestinal tract, to soils, rivers, and oceans. For the most part, bacteria are beneficial, acting to degrade organic waste and recycle nutrients back into the food chain. Sometimes, however, bacteria cause problems.

In order to prevent problems associated with bacteria, antibiotics are often added to an environment to suppress bacterial growth. While this treatment can be effective, the USDA has documented the emergence of antibiotic resistant bacterial strains. Since there are limited ways to treat or prevent bacterial contamination, antibiotic resistance would result in frequent problems associated with contamination such as spoilage. There is also a public health risk with the emergence of antibiotic resistance, because often the bacterial species that cause contamination are ubiquitous in the environment and inhabit the intestinal tract of vertebrate animals, including humans. These bacterial strains do cause human infections and such infections would be medically untreatable if they involve antibiotic resistant bacteria.

There is a need to develop methods to limit or eliminate bacterial contamination, are not cost prohibitive, and do not cause harm to the environment or potentially cause antibiotic resistant bacteria. Current methods are costly and may even introduce harmful antibiotic resistant bacteria to our environment. The present invention limits or eliminates bacteria growth and contamination, and provides a solution to the threats of antibiotic resistance emergence at a reasonable cost.

SUMMARY OF THE INVENTION

The present invention relates to any population of cells, whereby at least one cell comprises an antibacterial protein. One object of the present invention is to provide novel bactericidal yeast that reduces or eliminates bacterial contamination. Another object of the invention is to provide bactericidal yeast that expresses at least one antibacterial protein. A further object of the invention is to provide nucleic acid and amino acid sequences encoding antibacterial proteins that have been optimized for yeast expression. Specifically, the bactericidal yeast of the invention expresses an antibacterial protein. Preferably, a suitable antibacterial protein is encoded by an amino acid sequence having at least 65, 66, 70, 75, 80, 81, 82, 83, 84, 85, 86, 87, 88, 89, 90, 91, 92, 93, 94, 95, 96, 97, 98, 99%, or more identity to SEQ ID NO: 6, SEQ ID NO: 7, SEQ ID NO: 8, SEQ ID NO: 9, or SEQ ID NO: 10. Also, a suitable antibacterial protein is encoded by a nucleic acid sequence having at least 70, 75, 80, 81, 82, 83, 84, 85, 86, 87, 88, 89, 90, 91, 92, 93, 94, 95, 96, 97, 98, 99%, or more identity to SEQ ID NO: 1, SEQ ID NO: 2, SEQ ID NO: 3, SEQ ID NO: 4, or SEQ ID NO: 5.

A suitable population of cells may be prokaryotic or eukaryotic. Exemplary cell types include yeast, fungus, bacteria, insect, plant, or mammalian. Suitable yeast strains include, but are not limited to, *Kluyveromyces lactis, Saccharomyces cerevisiae, Schizosaccharomyces pombe*, and *Candida albicans*. Further, a population of cells may comprise an organism. Suitable organisms include yeast, plant, fungus, bacteria, and non-human mammalians. Preferably the organism is yeast. A suitable organism of the invention expresses an antibacterial protein. Preferably, the organism expresses at least one antibacterial protein having a nucleic acid sequence having at least 70, 75, 80, 81, 82, 83, 84, 85, 86, 87, 88, 89, 90, 91, 92, 93, 94, 95, 96, 97, 98, 99%, or more identity to SEQ ID NO: 1, SEQ ID NO: 2, SEQ ID NO: 3, SEQ ID NO: 4, or SEQ ID NO: 5. The organism may express at least one antibacterial protein having at least 65, 66, 70, 75, 80, 81, 82, 83, 84, 85, 86, 87, 88, 89, 90, 91, 92, 93, 94, 95, 96, 97, 98, 99%, or more identity to SEQ ID NO: 6, SEQ ID NO: 7, SEQ ID NO: 8, SEQ ID NO: 9, or SEQ ID NO: 10. The organism may express one, two, three, four, five, six, or more antibacterial proteins of the invention. Further, the expression of the antibacterial protein may be environmentally sensitive. A suitable sensitivity may include, but is not limited to, the presence of lactic acid or ethanol.

The invention also provides methods of protecting against bacterial contamination. A method of the invention includes adding bactericidal yeast expressing at least one antibacterial protein of the invention to an environment at risk of bacterial contamination. Another method of the invention includes adding bactericidal yeast expressing at least one antibacterial protein of the invention to a batch solution at risk of bacterial contamination. The batch solution may be in preparation of fermentation, whereby the bactericidal yeast is added as a fermentation ingredient.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION

Figure 1:
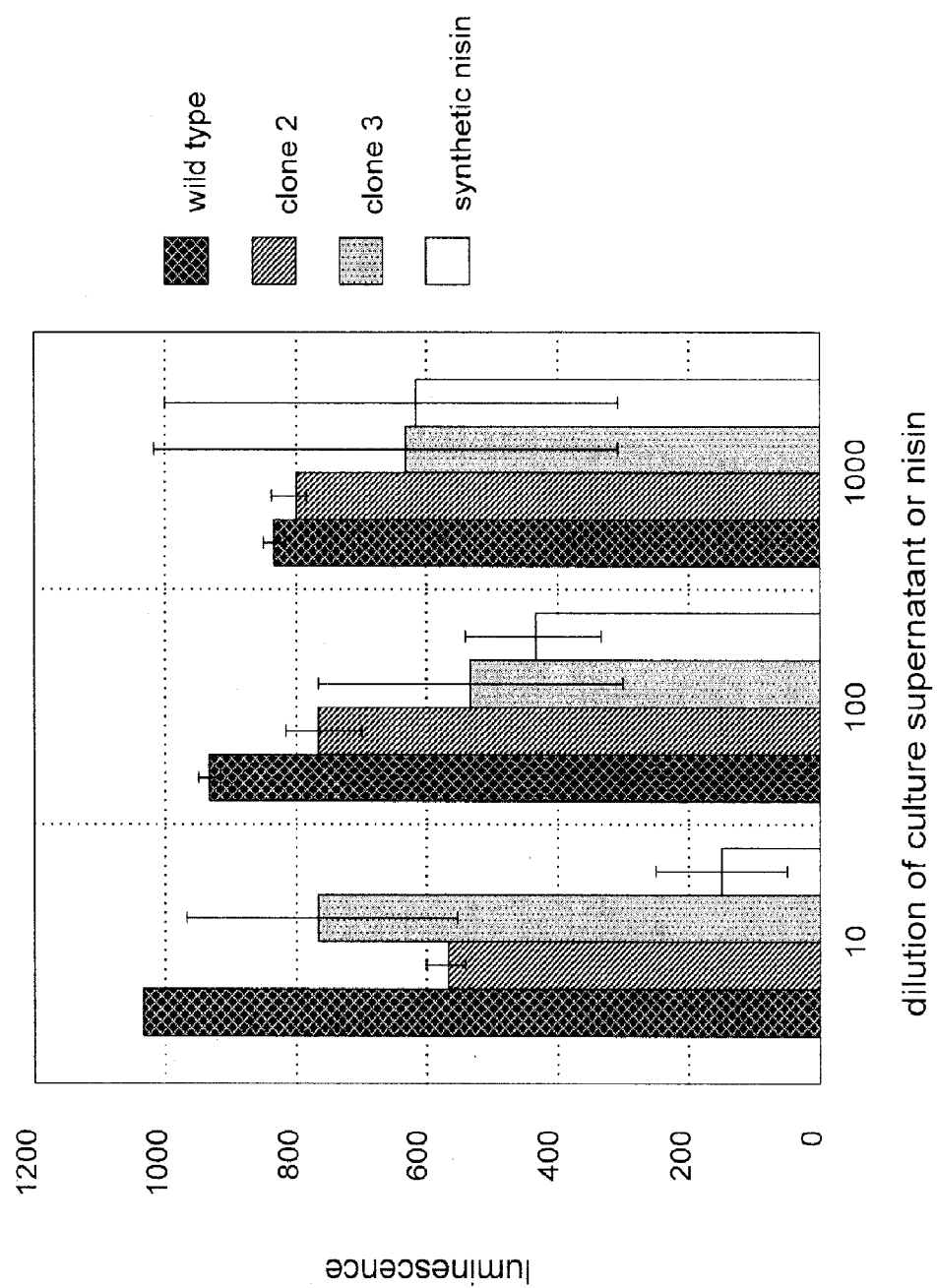
FIG. 1 shows the antibacterial activity of yeast expressing the nisin transgene.

The present invention relates to novel antibacterial proteins. Specifically, proteins having antibacterial activity once secreted from a population of cells or organisms. As such, the methods for use of the antibacterial proteins are also contemplated.

I. Antibacterial Proteins

A. Nucleic Acids Encoding Antibacterial Proteins

Nucleic acids encoding antibacterial proteins (APs) derived from bacteriophage genomes are disclosed. An AP nucleotide sequence includes an open reading frame that encodes at least a catalytic domain and a binding domain. In particular, an AP nucleic acid is capable, under appropriate conditions, of expressing a protein having antibacterial activity such as that illustrated by SEQ ID NOs: 1-10.

AP nucleotides further include nucleic acid sequences that hybridize under high stringency conditions to SEQ ID NOs: 1-5 such as those that are homologous, substantially similar, or identical to the nucleic acids of the present invention. Homologous nucleic acid sequences will have a sequence similarity of at least about 50%, 55%, 60%, 65%, 70%, 75%, 80%, 85%, 90%, 91%, 92%, 93%, 94%, 95%, 96%, 97%, 98%, 99%, or 100% to any of SEQ ID NOs: 1-5 or the respective complementary sequences. Sequence similarity may be calculated using a number of algorithms known in the art, such as BLAST, described in Altschul, S. F., et al., J. Mol. Biol. 215:403-10, 1990 (using default settings, i.e. parameters w=4 and T=17). The nucleic acids may differ in sequence from the above-described nucleic acids due to the degeneracy of the genetic code. In general, a reference sequence will be 18 nucleotides, more usually 30 or more nucleotides, and may comprise an entire AP sequence for comparison purposes.

Nucleotide sequences that can express an AP, or related protein, and hybridize to the listed nucleotide sequences are contemplated herein. Stringent hybridization conditions include conditions such as hybridization at 50° C. or higher and 0.1×SSC (15 mM sodium chloride/1.5 mM sodium citrate). Another example is overnight incubation at 42° C. in a solution of 50% formamide, 5×SSC (150 mM NaCl, 15 mM trisodium citrate), 50 mM sodium phosphate (pH7.6), 5×Denhardt's solution, 10% dextran sulfate, and 20 µg/ml denatured, sheared salmon sperm DNA, followed by washing in 0.1×SSC at about 65° C. Exemplary stringent hybridization conditions are hybridization conditions that are at least about 80%, 85%, 90%, or 95% as stringent as the above specific conditions. Other stringent hybridization conditions are known in the art and may also be employed to identify homologs of the nucleic acids of the invention (Current Protocols in Molecular Biology, Unit 6, pub. John Wiley & Sons, N.Y., 1989).

Mutant nucleotides of the AP proteins may be used, so long as mutants include nucleic acid sequences that encode functional AP proteins as described herein. The subject nucleic acids may be mutated to alter properties of the encoded protein such as expression properties, folding properties, and antibacterial activity. A skilled artisan will recognize that proteins encoded by nucleic acids encoding homologues or mutants may have the same antibacterial properties as those encoded by SEQ ID Nos: 1-5 or may have altered antibacterial properties. The DNA sequence or protein product of such a mutation will usually be substantially similar to the sequences provided herein and will differ by one or more nucleotides or amino acids. The sequence changes may be substitutions, insertions, deletions, or a combination thereof. Techniques for mutagenesis of cloned genes are known in the art. Methods for site specific mutagenesis may be found in Gustin et al., Biotechniques 14:22, 1993; Barany, Gene 37:111-23, 1985; Colicelli et al., Mol. Gen. Genet. 199:537-9, 1985; and Sambrook et al., Molecular Cloning: A Laboratory Manual, CSH Press 1989, pp. 15.3-15.108 and all incorporated herein by reference. Such mutated nucleic acid derivatives may be used to study structure-function relationships of a particular AP protein, or to alter properties of the protein that affect its function or regulation. In summary, the invention relates to AP coding sequences such as those of SEQ ID NOs: 1-5, and variants or mutants thereof. Also, the invention encompasses the intermediatary RNAs encoded by the described nucleic acid sequences and that translates into an AP of the invention.

1. Harmonization of Nucleic Acid Sequences Encoding APs

To circumvent problems associated with poor translation efficiency of non-mammalian derived mRNA in mammalian systems, strategies to harmonize proteins are often used. Harmonizing a protein involves optimizing the nucleotide codons encoding specific amino acids to those more likely to be used in the specific host's genes. For example, GGG, GGA, GGT, and GGC all encode the amino acid Glycine; however, GGT is more often used to encode Glycine in Kluyreromyces lactis genes than GGG (Table 1). To increase translation efficiency in yeast cells, at the Glycine position, GGG should be replaced with GGT. Strategies to harmonize proteins are well known in the art and described herein in the Examples.

The present invention provides nucleic acid sequences encoding AP proteins of the invention harmonized for expression in yeast. The nucleic acids SEQ ID NOs: 1-5 have been optimized using the preferred codons of yeast genes (Table 1-4) in order to increase protein translation in yeast systems. One skilled in the art will recognize that coding sequences may be optimized for use in any species through codon harmonization.

Preferred codons for protein expression for a wide variety of organisms may be obtained from publicly available codon usage databases. The Codon Usage Database is an extended worldwide web version of CUTG (Codon Usage Tabulated from GenBank) developed and maintained by Yasukazu Nakamura at The First Laboratory for Plant Gene Research, Kazusa DNA Research Institute, Japan. The KEGG (Kyoto Encyclopedia of Genes and Genomes) Database is another database and is described in Aoki and Kanehisa, Current Protocols in Bioinformatics, (2005) 1.12.1-1.12.54, which is incorporated herein by reference.

TABLE 1

Preferred DNA Codons for *Kluyreromyces lactis*.

| Amino Acid | Codon | Number | Frequency/1000 |
|---|---|---|---|
| Gly | GGG | 788.00 | 5.25 |
| Gly | GGA | 1727.00 | 11.50 |
| Gly | GGT | 5335.00 | 35.54 |
| Gly | GGC | 845.00 | 5.63 |
| Glu | GAG | 2393.00 | 15.94 |
| Glu | GAA | 7124.00 | 47.46 |
| Asp | GAT | 6116.00 | 40.74 |
| Asp | GAC | 2762.00 | 18.40 |
| Val | GTG | 1636.00 | 10.90 |
| Val | GTA | 1642.00 | 10.94 |
| Val | GTT | 3893.00 | 25.93 |
| Val | GTC | 2138.00 | 14.24 |
| Ala | GCG | 734.00 | 4.89 |
| Ala | GCA | 2334.00 | 15.55 |
| Ala | GCT | 4217.00 | 28.09 |
| Ala | GCC | 1778.00 | 11.84 |
| Arg | AGG | 902.00 | 6.01 |
| Arg | AGA | 3707.00 | 24.69 |
| Ser | AGT | 1917.00 | 12.77 |
| Ser | AGC | 953.00 | 6.35 |
| Lys | AAG | 5070.00 | 33.77 |

TABLE 1-continued

Preferred DNA Codons for *Kluyveromyces lactis*.

| Amino Acid | Codon | Number | Frequency/1000 |
|---|---|---|---|
| Lys | AAA | 5629.00 | 37.50 |
| Asn | AAT | 4735.00 | 31.54 |
| Asn | AAC | 3829.00 | 25.51 |
| Met | ATG | 3158.00 | 21.04 |
| Met | ATA | 2368.00 | 15.77 |
| Ile | ATT | 4123.00 | 27.46 |
| Ile | ATC | 3138.00 | 20.90 |
| Thr | ACG | 874.00 | 5.82 |
| Thr | ACA | 2282.00 | 15.20 |
| Thr | ACT | 3444.00 | 22.94 |
| Thr | ACC | 1923.00 | 12.81 |
| Trp | TGG | 1697.00 | 11.30 |
| Trp | TGA | 83.00 | 0.55 |
| Cys | TGT | 1433.00 | 9.55 |
| Cys | TGC | 483.00 | 3.22 |
| End | TAG | 55.00 | 0.37 |
| End | TAA | 163.00 | 1.09 |
| Tyr | TAT | 3033.00 | 20.20 |
| Tyr | TAC | 2557.00 | 17.03 |
| Leu | TTG | 5083.00 | 33.86 |
| Leu | TTA | 3534.00 | 23.54 |
| Phe | TTT | 2929.00 | 19.51 |
| Phe | TTC | 3534.00 | 23.54 |
| Ser | TCG | 1150.00 | 7.66 |
| Ser | TCA | 2445.00 | 16.29 |
| Ser | TCT | 4012.00 | 26.73 |
| Ser | TCC | 1901.00 | 12.66 |
| Arg | CGG | 224.00 | 1.49 |
| Arg | CGA | 318.00 | 2.12 |
| Arg | CGT | 1001.00 | 6.67 |
| Arg | CGC | 228.00 | 1.52 |
| Gln | CAG | 1769.00 | 11.78 |
| Gln | CAA | 4411.00 | 29.38 |
| His | CAT | 2130.00 | 14.19 |
| His | CAC | 1043.00 | 6.95 |
| Thr | CTG | 770.00 | 5.13 |
| Thr | CTA | 1766.00 | 11.76 |
| Thr | CTT | 1779.00 | 11.85 |
| Thr | CTC | 649.00 | 4.32 |
| Pro | CCG | 633.00 | 4.22 |
| Pro | CCA | 3201.00 | 21.32 |
| Pro | CCT | 2020.00 | 13.46 |
| Pro | CCC | 573.00 | 3.82 |

TABLE 2

Preferred DNA Codons for *Saccharomyces cerevisiae*.

| Amino Acid | Codon | Number | Frequency/1000 |
|---|---|---|---|
| Gly | GGG | 39359.00 | 6.02 |
| Gly | GGA | 71216.00 | 10.90 |
| Gly | GGT | 156109.00 | 23.89 |
| Gly | GGC | 63903.00 | 9.78 |
| Glu | GAG | 125717.00 | 19.24 |
| Glu | GAA | 297944.00 | 45.60 |
| Asp | GAT | 245641.00 | 37.59 |
| Asp | GAC | 132048.00 | 20.21 |
| Val | GTG | 70337.00 | 10.76 |
| Val | GTA | 76927.00 | 11.77 |
| Val | GTT | 144243.00 | 22.07 |
| Val | GTC | 76947.00 | 11.78 |
| Ala | GCG | 40358.00 | 6.18 |
| Ala | GCA | 105910.00 | 16.21 |
| Ala | GCT | 138358.00 | 21.17 |
| Ala | GCC | 82357.00 | 12.60 |
| Arg | AGG | 60289.00 | 9.23 |
| Arg | AGA | 139081.00 | 21.28 |
| Ser | AGT | 92466.00 | 14.15 |
| Ser | AGC | 63726.00 | 9.75 |
| Lys | AAG | 201361.00 | 30.82 |
| Lys | AAA | 273618.00 | 41.87 |
| Asn | AAT | 233124.00 | 35.68 |
| Asn | AAC | 162199.00 | 24.82 |
| Met | ATG | 136805.00 | 20.94 |
| Met | ATA | 116254.00 | 17.79 |
| Ile | ATT | 196893.00 | 30.13 |
| Ile | ATC | 112176.00 | 17.17 |
| Thr | ACG | 52045.00 | 7.96 |
| Thr | ACA | 116084.00 | 17.76 |
| Thr | ACT | 132522.00 | 20.28 |
| Thr | ACC | 83207.00 | 12.73 |
| Trp | TGG | 67789.00 | 10.37 |
| Trp | TGA | 4447.00 | 0.68 |
| Cys | TGT | 52903.00 | 8.10 |
| Cys | TGC | 31095.00 | 4.76 |
| End | TAG | 3312.00 | 0.51 |
| End | TAA | 6913.00 | 1.06 |
| Tyr | TAT | 122728.00 | 18.78 |
| Tyr | TAC | 96596.00 | 14.78 |
| Leu | TTG | 177573.00 | 27.17 |
| Leu | TTA | 170884.00 | 26.15 |
| Phe | TTT | 170666.00 | 26.12 |
| Phe | TTC | 120510.00 | 18.44 |
| Ser | TCG | 55951.00 | 8.56 |
| Ser | TCA | 122028.00 | 18.67 |
| Ser | TCT | 153557.00 | 23.50 |
| Ser | TCC | 92923.00 | 14.22 |
| Arg | CGG | 11351.00 | 1.74 |
| Arg | CGA | 19562.00 | 2.99 |
| Arg | CGT | 41791.00 | 6.40 |
| Arg | CGC | 16993.00 | 2.60 |
| Gln | CAG | 79121.00 | 12.11 |
| Gln | CAA | 178251.00 | 27.28 |
| His | CAT | 89007.00 | 13.62 |
| His | CAC | 50785.00 | 7.77 |
| Thr | CTG | 68494.00 | 10.48 |
| Thr | CTA | 87619.00 | 13.41 |
| Thr | CTT | 80076.00 | 12.25 |
| Thr | CTC | 35545.00 | 5.44 |
| Pro | CCG | 34597.00 | 5.29 |
| Pro | CCA | 119641.00 | 18.31 |
| Pro | CCT | 88263.00 | 13.51 |
| Pro | CCC | 44309.00 | 6.78 |

TABLE 3

Preferred DNA Codons for *Schizosaccharomyces pombe*.

| Amino Acid | Codon | Number | Frequency |
|---|---|---|---|
| Gly | GGG | 12611.00 | 4.41 |
| Gly | GGA | 45350.00 | 15.86 |
| Gly | GGT | 61455.00 | 21.49 |
| Gly | GGC | 23819.00 | 8.33 |
| Glu | GAG | 60189.00 | 21.05 |
| Glu | GAA | 126924.00 | 44.39 |
| Asp | GAT | 108632.00 | 37.99 |
| Asp | GAC | 44870.00 | 15.69 |
| Val | GTG | 23799.00 | 8.32 |
| Val | GTA | 35383.00 | 12.37 |
| Val | GTT | 82961.00 | 29.01 |
| Val | GTC | 30476.00 | 10.66 |
| Ala | GCG | 15402.00 | 5.39 |
| Ala | GCA | 45581.00 | 15.94 |
| Ala | GCT | 85195.00 | 29.79 |
| Ala | GCC | 32882.00 | 11.50 |
| Arg | AGG | 14555.00 | 5.09 |
| Arg | AGA | 32175.00 | 11.25 |
| Ser | AGT | 42557.00 | 14.88 |
| Ser | AGC | 26242.00 | 9.18 |
| Lys | AAG | 70110.00 | 24.52 |
| Lys | AAA | 113860.00 | 39.82 |
| Asn | AAT | 97492.00 | 34.10 |
| Asn | AAC | 51016.00 | 17.84 |
| Met | ATG | 59444.00 | 20.79 |

TABLE 3-continued

Preferred DNA Codons for *Schizosaccharomyces pombe*.

| Amino Acid | Codon | Number | Frequency |
|---|---|---|---|
| Met | ATA | 38588.00 | 13.50 |
| Ile | ATT | 100275.00 | 35.07 |
| Ile | ATC | 36129.00 | 12.64 |
| Thr | ACG | 18756.00 | 6.56 |
| Thr | ACA | 40864.00 | 14.29 |
| Thr | ACT | 65826.00 | 23.02 |
| Thr | ACC | 30616.00 | 10.71 |
| Trp | TGG | 31666.00 | 11.07 |
| Trp | TGA | 1228.00 | 0.43 |
| Cys | TGT | 25792.00 | 9.02 |
| Cys | TGC | 15958.00 | 5.58 |
| End | TAG | 1282.00 | 0.45 |
| End | TAA | 3622.00 | 1.27 |
| Tyr | TAT | 63277.00 | 22.13 |
| Tyr | TAC | 33662.00 | 11.77 |
| Leu | TTG | 68803.00 | 24.06 |
| Leu | TTA | 75328.00 | 26.34 |
| Phe | TTT | 92872.00 | 32.48 |
| Phe | TTC | 37197.00 | 13.01 |
| Ser | TCG | 23155.00 | 8.10 |
| Ser | TCA | 51773.00 | 18.11 |
| Ser | TCT | 86624.00 | 30.29 |
| Ser | TCC | 34753.00 | 12.15 |
| Arg | CGG | 8560.00 | 2.99 |
| Arg | CGA | 22918.00 | 8.01 |
| Arg | CGT | 44685.00 | 15.63 |
| Arg | CGC | 17213.00 | 6.02 |
| Gln | CAG | 31063.00 | 10.86 |
| Gln | CAA | 78435.00 | 27.43 |
| His | CAT | 46721.00 | 16.34 |
| His | CAC | 18013.00 | 6.30 |
| Thr | CTG | 18453.00 | 6.45 |
| Thr | CTA | 24965.00 | 8.73 |
| Thr | CTT | 72340.00 | 25.30 |
| Thr | CTC | 20752.00 | 7.26 |
| Pro | CCG | 13034.00 | 4.56 |
| Pro | CCA | 36383.00 | 12.72 |
| Pro | CCT | 61687.00 | 21.57 |
| Pro | CCC | 23151.00 | 8.10 |

TABLE 4

Preferred DNA Codons for *Candida albicans*.

| Amino Acid | Codon | Number | Frequency/1000 |
|---|---|---|---|
| Gly | GGG | 4945.00 | 7.78 |
| Gly | GGA | 8710.00 | 13.70 |
| Gly | GGT | 18556.00 | 29.19 |
| Gly | GGC | 2818.00 | 4.43 |
| Glu | GAG | 7547.00 | 11.87 |
| Glu | GAA | 31701.00 | 49.87 |
| Asp | GAT | 27797.00 | 43.73 |
| Asp | GAC | 8545.00 | 13.44 |
| Val | GTG | 6612.00 | 10.40 |
| Val | GTA | 5460.00 | 8.59 |
| Val | GTT | 19155.00 | 30.14 |
| Val | GTC | 5773.00 | 9.08 |
| Ala | GCG | 1346.00 | 2.12 |
| Ala | GCA | 10162.00 | 15.99 |
| Ala | GCT | 17393.00 | 27.36 |
| Ala | GCC | 7453.00 | 11.73 |
| Arg | AGG | 1834.00 | 2.89 |
| Arg | AGA | 13817.00 | 21.74 |
| Ser | AGT | 11094.00 | 17.45 |
| Ser | AGC | 2955.00 | 4.65 |
| Lys | AAG | 11660.00 | 18.34 |
| Lys | AAA | 31114.00 | 48.95 |
| Asn | AAT | 27162.00 | 42.73 |
| Asn | AAC | 11560.00 | 18.19 |
| Met | ATG | 11591.00 | 18.24 |
| Met | ATA | 9127.00 | 14.36 |
| Ile | ATT | 25761.00 | 40.53 |

TABLE 4-continued

Preferred DNA Codons for *Candida albicans*.

| Amino Acid | Codon | Number | Frequency/1000 |
|---|---|---|---|
| Ile | ATC | 8590.00 | 13.51 |
| Thr | ACG | 2501.00 | 3.93 |
| Thr | ACA | 11928.00 | 18.77 |
| Thr | ACT | 19438.00 | 30.58 |
| Thr | ACC | 8567.00 | 13.48 |
| Trp | TGG | 6942.00 | 10.92 |
| Trp | TGA | 180.00 | 0.28 |
| Cys | TGT | 5964.00 | 9.38 |
| Cys | TGC | 1135.00 | 1.79 |
| End | TAG | 336.00 | 0.53 |
| End | TAA | 632.00 | 0.99 |
| Tyr | TAT | 16146.00 | 25.40 |
| Tyr | TAC | 6614.00 | 10.41 |
| Leu | TTG | 21993.00 | 34.60 |
| Leu | TTA | 22928.00 | 36.07 |
| Phe | TTT | 18958.00 | 29.83 |
| Phe | TTC | 9899.00 | 15.57 |
| Ser | TCG | 4341.00 | 6.83 |
| Ser | TCA | 16751.00 | 26.35 |
| Ser | TCT | 13984.00 | 22.00 |
| Ser | TCC | 6145.00 | 9.67 |
| Arg | CGG | 604.00 | 0.95 |
| Arg | CGA | 2604.00 | 4.10 |
| Arg | CGT | 3791.00 | 5.96 |
| Arg | CGC | 523.00 | 0.82 |
| Gln | CAG | 4163.00 | 6.55 |
| Gln | CAA | 22696.00 | 35.71 |
| His | CAT | 9373.00 | 14.75 |
| His | CAC | 3578.00 | 5.63 |
| Thr | CTG | 2201.00 | 3.46 |
| Thr | CTA | 2782.00 | 4.38 |
| Thr | CTT | 6456.00 | 10.16 |
| Thr | CTC | 1636.00 | 2.57 |
| Pro | CCG | 1721.00 | 2.71 |
| Pro | CCA | 16709.00 | 26.29 |
| Pro | CCT | 8495.00 | 13.36 |
| Pro | CCC | 2665.00 | 4.19 |

B. Protein/Polypeptide Compositions

The invention contemplates antibacterial proteins (APs) and mutants thereof, which include those proteins encoded by the subject nucleic acids, as well as polypeptides comprising the antibacterial proteins. The isolated antibacterial proteins of the invention are exemplified by the sequences of SEQ ID NOs: 6-10. Further, the invention includes both the full-length proteins, as well as portions or fragments thereof.

Homologs or proteins (or fragments thereof) that vary in sequence from the amino acid sequences SEQ ID NOs: 6-10 are also included in the invention. By homolog is meant a protein having at least about 10%, usually at least about 25%, 30%, 40%, 45%, 50%, 55%, 60%, 65%, 70%, 75%, 80%, 85%, 90%, 95%, 99% or higher amino acid sequence identity to the proteins encoded by SEQ ID NOs: 5-10, as determined using MegAlign, DNAstar (1998) clustal algorithm as described in Higgins, D. G. and Sharp, P. M., Fast and Sensitive Multiple Sequence Alignments on a Microcomputer, CABIOS, 5: 151-153, 1989, both incorporated herein by reference.

APs of the invention may be mutated, or altered, to enhance, or change, biological properties of the protein. Such biological properties include, but are not limited to, in vivo or in vitro stability (e.g., half-life) and antibacterial activity. Suitable mutations include single amino acid changes, deletions of one or more amino acids, N-terminal truncations, C-terminal truncations, insertions, etc. Mutants can be generated using standard techniques of molecular biology, including random mutagenesis and targeted mutagenesis as described in Current Protocols in Molecular Biology, Unit 8, pub, John Wiley & Sons, Inc., 2000 and incorporated herein by reference.

Suitable mutants include an amino acid sequence encoded by an open reading frame (ORF) of the gene encoding the subject isolated protein, including the full length protein and fragments thereof, particularly biologically active fragments and fragments corresponding to functional domains, and the like; and including fusions of the subject polypeptides to other proteins or parts thereof. Fragments of interest will typically be at least about 10 amino acids (aa) in length, usually at least about 30, 40, or 50 aa in length, more preferably about 60, 70, 80, 90, 100, 110, 120, 130, 140, or 150 aa in length and may be as long as about 160, 170, 180, 190, 200, 220, 240, 260, 280 or 300 aa in length or even longer, but will usually not exceed about 450 aa in length, where the fragment will have a stretch of amino acids that is identical to the subject protein of at least about 10 aa, and usually at least about 15 aa, and in many embodiments at least about 50, 60, 70, 80, 90, 100, 110, 120, 130, 140, or 150 aa in length. The subject polypeptides can be about 25 aa, about 50 aa, about 75 aa, about 100 aa, about 125 aa, about 150 aa, about 200 aa, about 210 aa, about 220 aa, about 230 aa, or about 240 aa in length, up to and including the entire protein. A skilled artisan will recognize that a protein fragment may retain all or substantially all of a biological property of the isolated protein.

1. AP Characteristics

The proteins and polypeptides of the invention are characterized by having antibacterial activity. Further, the APs of the invention include at least 2 components: 1) a peptidoglycan-digesting catalytic domain, and 2) a cell-wall associated protein domain. Suitable catalytic domains include those of bacteriophage proteins that have the ability to facilitate the digestion, or destruction, of a peptidoglycan containing substance such as a bacterium cell wall. Exemplary catalytic domains include those of lysine enzymes such as, but are not limited to, the catalytic domain sequences of endo-beta-N-acetylglucosaminidase, endopeptidase, N-acetylmuramyl-L-alanine amidase, and muramidase. Further a suitable catalytic domain may be derived from any protein having a catalytic domain with catalytic activity specific to chemical bonds connecting molecules comprising bacterial cell walls. Preferably, the catalytic activity is specific to chemical bonds connecting molecules comprising Lactobacillaceae cell walls. More preferably, the catalytic activity is specific to bacteria cell walls and not yeast cell walls. More preferably, the catalytic activity is specific to Lactobacillaceae cell walls and not yeast cell walls. The catalytic domain of APs includes the amino acid residues at about positions 1-222 found in SEQ ID NOs: 6-10. A skilled artisan will appreciate that the catalytic domain may be mutated to alter antibacterial properties.

The antibacterial activity also depends, in part, upon the binding domain, which targets the protein to the cell wall of a bacterium. Once bound to the bacterium the catalytic domain facilitates the destruction of the cell wall, ultimately destroying the bacteria. A suitable binding domain includes those that cause the catalytic domain to attach to a cell wall so that the catalytic domain can digest the molecules of the cell wall. Exemplary binding domains include, but are not limited to, those derived from viral pathogens such as Lactobacillaceae viral pathogens. The binding domain of the APs of the invention includes the amino acid residues at about positions 204-280 found in SEQ ID NOs: 6-10. A skilled artisan will appreciate that the binding domain may be mutated to alter antibacterial properties.

Further, the APs of the invention may contain sequence that allows proper folding of the protein. Exemplary sequence includes at least one amino acid or more such that the AP retains antibacterial activity. The sequences of SEQ ID Nos: 6-10 contain a flexible hinge sequence that allows proper folding. The flexible hinge sequence includes the amino acid residues GGGGSGGGGSGGGGS positioned between the catalytic domain sequence and the binding domain sequence. A skilled artisan will recognize that any number of different sequence compositions and lengths may be used to allow proper folding of the catalytic domain and binding domain.

The APs of the invention may further include additional components that enhance its expression. Such additional components include promoters, enhancers, secretion signals, etc. For example, the AP sequence may include a host specific secretion signal. An exemplary secretion signal would include, but is not limited to, a yeast signal peptide sequence that mediates secretion of the AP gene product. Further, the AP sequence may include, or be under the control of an inducible or constitutive promoter. Such promoters may be environmentally-sensitive to specific substances. By way of example, a promoter may be sensitive to lactic acid, such as the LDH promoter. In the presence of lactic acid, the promoter activates transcription of the downstream gene. Likewise, a promoter may be activated by a transcription factor that is sensitive to a substance, such as the alcohol dehydrogenase I promoter of *Aspergillus nidulans*. In the presense of ethanol, the alcR transcription factor binds to the alcA binding domain in the alcohol dehydrogenase I promoter and activates transcription of the downstream gene. Methods for using inducible promoters are described in the art as well as in the Examples herein.

The subject proteins typically range in length from about 200 to 500 residues and included herein are specific examples that are about 244, 300, 303, 244, 451, 480, and 483 amino acid residues in length. The subject proteins include both shorter and longer variants that range in length from as short as about 50, 100, 120, 140, 150, 155, 160, 165, 170, 175, 180, 185, 190, 200, or 205 to as long as about 230, 235, 240, 245, 250, 255, 260, 265, 270, 275, 280, 285, 290, 295 or even longer. The subject proteins generally have a molecular weight ranging from about 15 to 55 kDa, including specifically 19.2, 20.1, 26.4, 28.8, 32.5, 48.0, and 51.4 kDa.

2. AP Production

The present invention includes a method of producing an AP by cultivating a host cell expressing an AP and then isolating the protein. Such methods include the introduction of an expression vector containing at least one protein coding sequence of the invention into a host cell, as described herein, cultivation of the subject protein containing host cell, and isolation of the subject protein from the cell extract. The expressed subject protein may or may not be linked to another protein of interest. Methods to cultivate host cells are known in the art. Methods to express and isolate a subject protein are described in Current Protocols in Protein Science, Units 5, pub. John Wiley & Sons, Inc., 2002 and Current Protocols in Protein Science, Units 6, pub. John Wiley & Sons, Inc., 2002 and both are incorporated herein by reference.

C. Expression System for APs

1. Vectors

Methods for introducing a DNA sequence into eukaryotic cells are known in the art and typically include the use of a DNA vector or plasmid. There are many vectors known and available in the art that are useful for the polynucleotides of the invention. One of skill in the art will recognize that the selection of a particular vector depends upon the intended use of the polynucleotide. Preferably, the DNA sequences are introduced by a vector or plasmid, capable of transforming and driving the expression of the components of the construct in the desired cell type, whether that cell type is prokaryotic or eukaryotic. Many vectors comprise sequences allowing both prokaryotic vector replication and eukaryotic expression of operably linked gene sequences.

Vectors useful according to the invention may be autonomously replicating, that is, the vector exists extrachromosomally, and its replication is not necessarily directly linked to the replication of the host genome. Alternatively, the replication of the vector may be linked to the replication of the host chromosomal DNA. For example, the vector may be integrated into a chromosome of the host cell as achieved by retroviral vectors.

A vector will comprise sequences operably linked to the coding sequence of the subject polypeptide that permit the transcription and translation of the components when appropriate. Within the expression vector, a subject polynucleotide is linked to a regulatory sequence as appropriate to obtain the desired expression properties. These regulatory sequences may include promoters (attached either at the 5' end of the sense strand or at the 3' end of the antisense strand), enhancers, terminators, operators, repressors, and inducers. The promoters may be regulated or constitutive. In some situations it may be desirable to use conditionally active promoters, such as environment specific promoters. In other words, the expression vector will provide a transcriptional and translational initiation region, which may be inducible or constitutive, where the coding region is operably linked under the transcriptional control of the transcriptional initiation region, and a transcriptional and translational termination region. These control regions may be native to the subject species from which the subject nucleic acid is obtained, or may be derived from exogenous sources.

Expression vectors generally have convenient restriction sites located near the promoter sequence to provide for the insertion of nucleic acid sequences encoding heterologous proteins. A selectable marker operative in the expression host may be present. Expression vectors may be used for, among other things, the production of fusion proteins, as is known in the art.

A skilled artisan will recognize that the choice of vector for use with the invention is dependent on the host with which the invention will be utilized. Suitable vectors include, but are not limited to, bacteriophage-derived vectors, viral vectors, retroviral vectors, adenoviral vectors, adeno-associated viral vectors, herpesviral vectors, and insect vector systems. Such vectors are well known in the art.

2. Expression Cassettes

Expression cassettes may include a transcription initiation region, at least one polynucleotide of the invention, and a transcriptional termination region. Of particular interest is the use of sequences that allow for the expression of functional epitopes or domains, usually at least about 8 amino acids in length, more usually at least about 15 amino acids in length, to about 25 amino acids, and up to the complete open reading frame of the polynucleotides of the invention. After introduction of the DNA, the cells containing the construct may be selected by means of a selectable marker, the cells expanded and then are used for expression.

3. Constructs

The term "construct" as used herein refers to a nucleic acid sequence containing at least one AP polynucleotide of the invention operably linked or fused to additional nucleic acids. Such constructs include vectors, plasmids, and expression cassettes encoding at least one polynucleotide of the invention. Constructs may be polynucleotides of the invention fused to other protein coding sequence to generate fusion proteins as described herein. For example, a polynucleotide may be operably linked or fused to a nucleotide sequence encoding a luciferase, luciferin, fluorescence tag, or other identifiable label known in the art.

4. Host Cells

Any cell into which a construct of the invention may be introduced and expressed is useful according to the invention. That is, because of the wide variety of uses for the constructs of the invention, any cell in which a construct of the invention may be expressed, and preferably detected, is a suitable host. The construct may exist in a host cell as an extrachromosomal element or be integrated into the host genome.

Host cells may be prokaryotic, such as any of a number of bacterial strains, or may be eukaryotic, such as yeast or other fungal cells, insect, plant, amphibian, or mammalian cells including, for example, rodent, simian or human cells. Host cells may be primary cultured cells, for example primary human fibroblasts or keratinocytes, or may be an established cell line, such as NIH3T3, 293T or CHO cells among others. Further, mammalian cells useful for expression of the constructs may be phenotypically normal or oncogenically transformed. It is assumed that one skilled in the art can readily establish and maintain a chosen host cell type in culture.

For large scale production of the protein, a unicellular organism, such as *E. coli, B. subtilis, S. cerevisiae*, insect cells in combination with baculovirus vectors, or cells of a higher organism such as vertebrates, e.g. COS 7 cells, HEK 293, CHO, *Xenopus* Oocytes, etc., may be used as the expression host cells. In some situations, it is desirable to express the construct in eukaryotic cells, where the expressed protein will benefit from native folding and post-translational modifications. Small peptides may also be synthesized in the laboratory. Polypeptides that are subsets of the complete protein sequence may be used to identify and investigate parts of the protein important for function. Specific expression systems of interest include bacterial, yeast, insect cell, and mammalian cell derived expression systems such as those described in U.S. Pat. No. 6,969,597 and incorporated herein by reference.

In a preferred embodiment, the proteins of the invention are expressed in yeast. Suitable yeast species include those known in the art. Exemplary yeast species include, but are not limited to, *Saccharomyces* species, *Cryptococcus species, Kluyveromyces* species, *Sporobolomyces* species, *Rhodotorula* species, *Brettanomyces* species, *Zygosaccharomyces* species, *Aureobasidium* species, and others known in the art. Exemplary species types include *Saccharomyces cerevisiae, Kluyveromyces lactis, Schizosaccharomyces pombe, Candida albicans, Saccharomyces pastorianus, Saccharomyces exiguous, Yarrowia lipolytica*, genetically engineered yeast including those engineered to ferment xylose, *Brettanomyces bruxellensis, Candida stellata, Torulaspora delbrueckii, Zygosaccharomyces bailii, Saccharomyces boulardii, Rhodotorula rubra, Rhodotorula glutinis, Rhodotorula marina, Rhodotorula aurantiaca, Cryptococcus albidus, Cryptococcus diffluens, Cryptococcus laurentii, Saccharomyces rosei, Saccharomyces pretoriensis, Saccharomyces cerevisiae, Sporobolomyces rosues, Sporobolomyces odorus, Kluyveromyces veronae, Aureobasidium pollulans* and others known in the art. A skilled artisan will recognize that the choice of yeast species depends upon the intended use since each yeast species has different physiological and fermentative properties.

When any of the above host cells, or other appropriate host cells or organisms, are used to replicate or express the polynucleotides or nucleic acids of the invention, the resulting replicated nucleic acid, RNA, expressed protein or polypeptide, is within the scope of the invention as a product of the host cell or organism. The product may be recovered by any appropriate means known in the art.

5. Introduction of Constructs to Host Cells

Constructs provided by the invention, including vectors, plasmids, and expression cassettes containing polynucleotides of the invention, may be introduced to selected host cells by any of a number of suitable methods known to those skilled in the art. Constructs may be inserted into mammalian host cells by methods including, but not limited to, electroporation, transfection, microinjection, micro-vessel transfer, particle bombardment, biolistic particle delivery, liposome mediated transfer and other methods described in Current Protocols in Cell Biology, Unit 20, pub. John Wiley & Sons, Inc., 2004 and incorporated herein by reference.

For example, for the introduction of a construct containing vectors into yeast or other fungal cells, chemical transformation methods are generally used (as described by Rose et al., 1990, Methods in Yeast Genetics, Cold Spring Harbor Laboratory Press, Cold Spring Harbor, N.Y. and incorporated herein by reference). For transformation of S. cerevisiae, for example, the cells are treated with lithium acetate. Transformed cells are then isolated on selective media appropriate to the selectable marker used. Other methods known in the art may be used as well as those described in the Examples herein.

Constructs may be introduced to appropriate bacterial cells by infection, as in the case of E. coli bacteriophage vector particles such as lambda or M13, or by any of a number of transformation methods for plasmid vectors or for bacteriophage DNA. For example, standard calcium-chloride-mediated bacterial transformation is still commonly used to introduce naked DNA to bacteria (Sambrook et al., 1989, Molecular Cloning, A Laboratory Manual, Cold Spring Harbor Laboratory Press, Cold Spring Harbor, N.Y., incorporated herein by reference), electroporation may also be used (Current Protocols in Molecular Biology, pub. John Wiley & Sons, Inc., 1993 and incorporated herein by reference).

For the introduction into insect cells, liposome-mediated transfection is commonly used, as is baculovirus infection. Cells such as Schneider-2 cells (*Drosophila melanogaster*), Sf-9 and Sf-21 cells (*Spodoptera frugiperda*) or High Five™ cells (*Trichoplusia ni*) may be transfected using any of a number of commercially available liposome transfection reagents optimized for use with insect cells. Additionally, particle bombardment, biolistic particle delivery, and microinjection are widely used to transform insects.

II. Methods of Use

A skilled artisan will recognize that the AP proteins of the invention have many potential uses. Specifically, the expression of the AP proteins by host cells is useful in situations in which the environment of the host cell has the potential of becoming contaminated by bacteria. By way of example, the AP proteins may be particularly useful in the science, food, energy, and pharmaceutical industries. By further example, the AP proteins may be used for, but not limited to, the following products: wine production, beer production, spirit production (i.e. whiskey), beverages, carbonated beverages, food, probiotic supplements, nutritional supplements, nutritional yeast products, bioremediation, ethanol production, as biosensors, screening assays, human or animal pharmaceuticals, medical purposes, dental purposes, such as prevention of tooth decay, and other uses.

A method of the invention includes providing a bactericidal organism to an environment at risk of bacterial contamination. Suitable environments include those in which the organism is viable. A skilled artisan will recognize that the environment may be limited by the nutrients required by the bactericidal organism. Preferably, the bactericidal organism is yeast.

Another method of the invention includes providing a bactericidal organism to a batch solution. Suitable batch solutions include those in which the organism is viable. Exemplary batch solutions include, but are not limited to, solutions prepared for fermentation processing and solutions at risk of contamination. A skilled artisan will recognize that the environment may be limited by the nutrients required by the bactericidal organism. Preferably, the bactericidal organism is yeast.

DEFINITIONS

As used herein, the term "bactericidal" refers to the expression of an antibacterial protein. The term is used herein to describe populations of cells and organisms that express at least one antibacterial protein of the invention.

The term "harmonization" or "harmonizing" or their variants refer to altering the nucleotide codons encoding specific amino acids to those more likely to be used in the host cell or organism without altering the encoded amino acid.

An "amino acid (aminocarboxylic acid)" is a component of proteins and peptides. All amino acids contain a central carbon atom to which an amino group, a carboxyl group, and a hydrogen atom are attached. Joining together amino acids forms polypeptides. "Polypeptides" are molecules containing up to 1000 amino acids. "Proteins" are polypeptide polymers containing 50 or more amino acids.

A "gene" is a hereditary unit that has one or more specific effects upon the phenotype of the organism; and the gene can mutate to various allelic forms. The gene is generally comprised of DNA.

The term "variant" relates to nucleotide or amino acid sequences which have similar sequences and that function in the same way.

A "host" is a cell or organism that receives a foreign biological molecule, including a genetic construct or antibody, such as a vector containing a gene.

A "nucleotide sequence" or "nucleic acid molecule" is a nucleotide polymer including genes, gene fragments, oligonucleotides, polynucleotides, and other nucleic acid sequences. "Nucleic acid" refers to the monomeric units from which DNA or RNA polymers are constructed, wherein the unit consists of a purine or pyrimidine base, a pentose, and a phosphoric acid group.

"Plasmids" are double-stranded, closed DNA molecules. Plasmids or "expression vectors" can contain coding sequences for expression machinery such as promoters, poly-A tails, stop codons, and other components necessary for expression of an inserted gene. Plasmids are used as vectors for transfecting a host with a nucleic acid molecule.

A "vector" is a replicon, such as plasmid, phage or cosmid, to which another DNA segment may be attached so as to bring about the replication of the attached segment.

A "population of cells" includes any cell or group of cells. A population of cells may include one or more stem cells and/or one or more progeny cells of a stem cell. Such population of cells can comprise a cell in culture, comprise in vitro tissue, or comprise a tissue within a living organism. The population of cells may be mammalian and includes, but is not limited to, yeast, murine, human, bovine, porcine, equine, ovine, or canine.

A "DNA molecule" refers to the polymeric form of deoxyribonucleotides (adenine, guanine, thymine, or cytosine) in either single stranded form or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes.

A DNA "coding sequence" is a DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and synthetic DNA sequences. A polyadenylation signal and transcription termination sequence may be located 3' to the coding sequence.

As used herein, the term "hybridization" refers to the process of association of two nucleic acid strands to form an antiparallel duplex stabilized by means of hydrogen bonding between residues of the opposite nucleic acid strands.

The term "oligonucleotide" refers to a short (under 100 bases in length) nucleic acid molecule.

"DNA regulatory sequences", as used herein, are transcriptional and translational control sequences, such as promoters, enhancers, polyadenylation signals, terminators, and the like, that provide for and/or regulate expression of a coding sequence in a host cell.

A "promoter sequence" is a DNA regulatory region capable of being bound by RNA polymerase, whereby the polymerase initiates transcription of a downstream (3' direction) coding sequence. For purposes of defining the present invention, the promoter sequence includes the minimum number of bases or elements necessary to initiate transcription at levels detectable above background. Within the promoter sequence will be found a transcription initiation site, as well as protein binding domains responsible for the binding of RNA polymerase. Various promoters, including inducible promoters, may be used to drive the various vectors of the present invention.

As used herein, the terms "restriction endonucleases" and "restriction enzymes" refer to enzymes that cut double-stranded DNA at or near a specific nucleotide sequence.

A cell has been "transformed" or "transfected" by exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. In another example, heterologous DNA includes coding sequence in a construct where portions of genes from two different sources have been brought together so as to produce a fusion protein product. Allelic variations or naturally-occurring mutational events do not give rise to a heterologous region of DNA as defined herein.

The amino acids described herein are preferred to be in the "L" isomeric form. The amino acid sequences are given in one-letter code (A: alanine; C: cysteine; D: aspartic acid; E: glutamic acid; F: phenylalanine; G: glycine; H: histidine; I: isoleucine; K: lysine; L: leucine; M: methionine; N: asparagine; P: proline; Q: glutamine; R: arginine; S: serine; T: threonine; V: valine; W: tryptophan; Y: tyrosine; X: any residue).

The term "specific binding," in the context of antibody binding to an antigen, is a term well understood in the art and refers to binding of an antibody to the antigen to which the antibody was raised, but not other, unrelated antigens.

As used herein the term "isolated" is meant to describe a polynucleotide, a nucleic acid, a protein, a polypeptide, an antibody, or a host cell that is in an environment different from that in which the polynucleotide, nucleic acid, protein, polypeptide, antibody, or host cell naturally occurs. In reference to a sequence, such as nucleic acid or amino acid, "isolated" includes sequences that are assembled, synthesized, amplified, or otherwise engineered by methods known in the art.

As used herein, the phrase "stringent hybridization conditions" refers to conditions under which a probe, primer or oligonucleotide will hybridize to its target sequence, but to no other sequences. Stringent conditions are sequence-dependent and will be different in different circumstances. Longer sequences hybridize specifically at higher temperatures than shorter sequences. Generally, stringent conditions are selected to be about 5° C. lower than the thermal melting point (Tm) for the specific sequence at a defined ionic strength and pH. The Tm is the temperature (under defined ionic strength, pH and nucleic acid concentration) at which 50% of the probes complementary to the target sequence hybridize to the target sequence at equilibrium. Since the target sequences are generally present in excess at Tm, 50% of the probes are occupied at equilibrium. Typically, stringent conditions will be those in which the salt concentration is less than about 1.0 M sodium ion, typically about 0.01 to 1.0 M sodium ion (or other salts) at pH 7.0 to 8.3 and the temperature is at least about 30° C. for short probes, primers or oligonucleotides (e.g., 10 nt to 50 nt) and at least about 60° C. for longer probes, primers and oligonucleotides. Stringent conditions may also be achieved with the addition of destabilizing agents, such as formamide. Preferably, the conditions are such that sequences at least about 65%, 70%, 75%, 85%, 90%, 95%, 98%, or 99% homologous to each other typically remain hybridized to each other.

The term "identity" in the context of sequences refers to the relatedness of two sequences on a nucleotide-by-nucleotide basis or amino acid-by-amino acid basis over a particular comparison window or segment. Thus, identity is defined as the degree of sameness, correspondence, or equivalence between the same strands (either sense or antisense) of two DNA segments or the primary structure of two polypeptides.

"Similarity" between two amino acid sequences is defined as the presence of a series of identical as well as conserved amino acid residues in both sequences. The higher the degree of similarity between two amino acid sequences, the higher the correspondence, sameness or equivalence of the two sequences. "Identity between two amino acid sequences" is defined as the presence of a series of exactly alike or invariant amino acid residues in both sequences. The percentage of sequence identity is calculated by comparing two optimally aligned sequences over a particular region, determining the number of positions at which the identical base occurs in both sequence in order to yield the number of matched positions, dividing the number of such positions by the total number of positions in the segment being compared and multiplying the result by 100. Optimal alignment of sequences may be conducted by the algorithm of Smith & Waterman, Appl. Math. 2:482 (1981), by the algorithm of Needleman & Wunsch, J. Mol. Biol. 48:443 (1970), by the method of Pearson & Lipman, Proc. Natl. Acad. Sci. (USA) 85:2444 (1988) and by computer programs which implement the relevant algorithms (e.g., Clustal Macaw Pileup, FASTDB (Intelligenetics), BLAST (National Center for Biomedical Information; Altschul et al., Nucleic Acids Research 25:3389 3402 (1997)), PILEUP (Genetics Computer Group, Madison, Wis.) or GAP, BESTFIT, FASTA and TFASTA (Wisconsin Genetics Software Package Release 7.0, Genetics Computer Group, Madison, Wis.). (U.S. Pat. No. 5,912,120.)

For purposes of the present invention, "complementarity" is defined as the degree of relatedness between two DNA segments. It is determined by measuring the ability of the sense strand of one DNA segment to hybridize with the antisense strand of the other DNA segment, under appropriate conditions, to form a double helix. In the double helix, adenine appears in one strand, thymine appears in the other strand. Similarly, wherever guanine is found in one strand, cytosine is found in the other. The greater the relatedness between the nucleotide sequences of two DNA segments, the greater the ability to form hybrid duplexes between the strands of the two DNA segments.

The terms "homology", "homologous," "substantially similar," and "corresponding substantially" are used interchangeably. They refer to sequence fragments, nucleic acid or amino acid, wherein changes in one or more bases or residues does not affect the ability of the fragment to result in a specific functional protein. These terms also refer to modifications of the nucleic acid or amino acid sequences of the instant invention such as deletion or insertion of one or more nucleotides or residues that do not substantially alter the functional properties of the resulting sequence relative to the initial, unmodified sequence. It is therefore understood, as those skilled in the art will appreciate, that the invention encompasses more than the specific exemplary sequences.

The term "operably linked" or "operatively linked" refers to the association of nucleic acid sequences on a single nucleic acid fragment so that the function of one is regulated by the other or is not hindered by the other. For example, a promoter is operably linked with a coding sequence when it is capable of regulating the expression of that coding sequence (i.e., that the coding sequence is under the transcriptional control of the promoter). Coding sequences can be operably linked to regulatory sequences in a sense or antisense orientation. In another example, two proteins can be operably linked, such that the function of either protein is not compromised. Generally, operably linked means that the nucleic acid sequences being linked are contiguous and, where necessary to join two protein coding regions, contiguous and in the same reading frame.

The term "expression", as used herein, refers to the production of a functional end-product.

By "substantially the same length" is meant that any difference in length does not exceed about 20%, usually does not exceed about 10% and more usually does not exceed about 5%; and have sequence identity to any of these sequences of at least about 80%, 85%, 90%, 95%, and usually at least about 99% over the entire length of the nucleic acid.

The term "polypeptide composition" as used herein refers to both the full-length protein, as well as portions or fragments thereof. Also included in this term are variations of the naturally occurring protein, where such variations are homologous or substantially similar to the naturally occurring protein, and mutants of the naturally occurring proteins, as described herein.

The term "effective amount" refers to the amount necessary to elicit a change in the environment or solution. For example, an effective amount of bactericidal yeast added to an environment would result in a reduction, elimination, or prevention of contamination.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Generation of Antibacterial Proteins

The amino acid sequences of the APs were designed based on multiple alignments of bacteriophage genes. There are four families of lysin catalytic domains found in enzymes of Lactobacillaceae specific bacteriophages. At least one AP of the invention was derived from each of the four families of catalytic domains.

The amino acid sequences were derived from between 8 and 20 full-length protein sequences containing catalytic domains, obtained from the public domain PFAM database. Each sequence was truncated from the caroboxy terminus so that only the catalytic domain sequence remained. If the sequence contained a bacterial secretion leader sequence, it was also truncated from the catalytic domain. The catalytic domain sequence sets were computationally aligned using a dynamic programming implementation of the ClustalW algorithm in the licensed software package CLC Combined Workbench (CLC bio) with default settings (FIGS. 6, 8, and 10). The resulting consensus sequence for each of the four catalytic domain families was used as the basis for each antibacterial protein of the invention. The consensus sequences were analyzed for secondary protein structure, also using the CLC program with default settings. Where a consensus sequence contained an ambiguity or gap, knowledge of the secondary protein structure was used to choose an amino acid for that position that would preserve the integrity of the secondary structure. The catalytic domain sequences are shown in FIGS. 5, 7, 9, and 11.

In addition to a catalytic domain, a carboxy terminal binding domain was also added to each AP of the invention. The binding domain provides a means for the AP to attach to the cell wall of a bacterium so that the catalytic domain can digest the molecules of the cell wall. A consensus sequence for a binding domain derived from Lactobacillaceae bacteriophages was constructed as described above for the catalytic domain. LysM is the common domain pattern found in Lactobacillaceae bacteriophages. Again, where the consensus sequence contained an ambiguity or gap, knowledge of the secondary protein structure was used to choose an amino acid for that position that would preserve the integrity of the secondary structure. The binding domain consensus sequence was added to the carboxy terminus of the catalytic domain consensus sequences.

The constructed amino acid sequences were then reverse translated using the codon frequency table for the yeast *Kluyveromyces lactis* (Table 1). Further adjustments to the nucleotide composition were made to optimize CG %, eliminate repeated nucleotides, and minimize secondary nucleic acid structure. Restriction enzyme sites were added for cloning purposes including a 5 prime XhoI site and a 3 prime BglII site. The optimized sequences were commercially synthesized and cloned into pUC57 plasmids. DNA was isolated from the pUC57 plasmids, digested with XhoI and BglII, and cloned into the yeast expression plasmid pKLAC1.

Example 2

Nisin Protein Synthesis

Nisin is an antibacterial bacteriocin substance that is secreted by some strains of *Lactococcus lactis* (*L. lactis*) bacteria. Nisin A (or nisin Z, which differs by a single amino acid from nisin A) is synthesized as a precursor peptide but then undergoes extensive, covalent, enzymatic modification to become an antibiotic molecule. The antibiotic final form of nisin is secreted by *L. lactis* to kill competing lactic acid bacteria in their local environment. Nisin is a commercial product used widely in the food and beverage industries. It has Generally Regarded As Safe (GRAS) status under US FDA regulations.

To demonstrate proof of principle for the use of bacteriocins secreted by genetically engineered yeast in protecting against bacterial contamination, the nisin A gene was cloned into the genome of the yeast *Kluyveromyces lactis*. Because yeast do not have the enzymes necessary to convert nisin peptide into the antibiotic chemical form, it was not anticipated that the nisin A peptide would have antibacterial activity. However, preparations from the nisin A containing yeast were found to have antibacterial activity when tested in a bacterial killing assay. Specifically, nisin A yeast preparations killed the target *Enterococcus faecalis* bacteria in a dose dependent manner, while preparations from non-engineered yeast did not.

The unmodified nisin gene was constructed using oligonucleotides that were commercially synthesized where the nisin peptide open reading frame was flanked with a 5 prime XhoI-Kex cleavage site and a 3 prime StuI site using internal overlapping cohesive ends. The open reading frame of the nisin peptide was codon harmonized according to *Kluyveromyces lactis* codon usage frequency (Table 1, SEQ ID NO. 10). The oligos were annealed, phosphorylated, ligated, and then the single double-stranded molecule was ligated into the commercial pKLAC1 yeast expression vector.

Example 3

General Cloning and Expression of AP Proteins

The antibacterial proteins of the invention were cloned into a yeast expression system and analyzed for antibacterial activity. The commercial yeast expression system (New England Biolabs) for *Kluyveromyces lactis* with the pKLAC1 shuttle vector was used. An AP to be expressed was cloned into the multiple cloning site of the pKLAC1 plasmid at the XhoI and BGLII restriction sites. The AP codons were placed in frame with both the KEX protease recognition site (amino acids lysine-arginine) and the preceding alpha mating factor secretion peptide so that the yeast would correctly process and secrete the AP. After cloning the AP gene into pKLAC1 in frame, the plasmid was amplified in *E. coli* host cells using ampicillin selection. Extracted plasmid was then linearized with the restriction enzyme SacII, which exposed the DNA sequence homologous with the *K. lactis* LAC4 at both the 5 prime and 3 prime termini of the vector. Specifically, 2 µg of pKLAC1 DNA containing an AP of interest was digested with 20 units of SacII in 50 µl of 1× NEBuffer at 37° C. for 2 hours. The digested DNA was desalted using a commercially available DNA fragment purification kit.

Introduction of the linearized expression cassette into *K. lactis* cells was achieved by chemical transformation using *K. lactis* GG799 Competent Cells and NEB Yeast Transformation Reagent. Specifically, 620 µl of NEB Yeast Transformation Reagent was added to *K. lactis* competent cells on ice. About 1 µg of linearized pKLAC1 DNA containing the AP of interest was added to the cell mixture, which was then incubated at 30° C. for 30 minutes. The cell mixture was heat shocked by incubating it at 37° C. for 1 hour in a water bath. The cells were pelleted by microcentrifugation at about 7000 r.p.m. for 2 minutes and the supernatant was discarded. The cell pellet was resuspended in 1 mL of sterile deionized water. The cells were again microcentrifuged at about 7000 r.p.m. for 2 minutes and the supernatant was discarded. The cells were then resuspended in 1 mL YPGlu medium and transferred to a sterile culture tube and incubated at 30° C. while shaking for 30 minutes. The cells were pelleted by microcentrifugation as described above and resuspended in 1 mL of sterile deionized water. The resuspended cells were plated onto separate YCB Agar Medium plates containing 5 mM acetamide and incubated at 30° C. for 3 to 4 days until colonies formed. Only the yeast that recombined the AP vector sequence into the endogenous LAC4 promoter, via homologous recombination, were able to utilize acetamide as a nitrogen source due to the presence of the acetamidase enzyme transgene in the vector. AP expression was driven by the constitutive expression of the LAC4 gene in the yeast.

Figure 2:
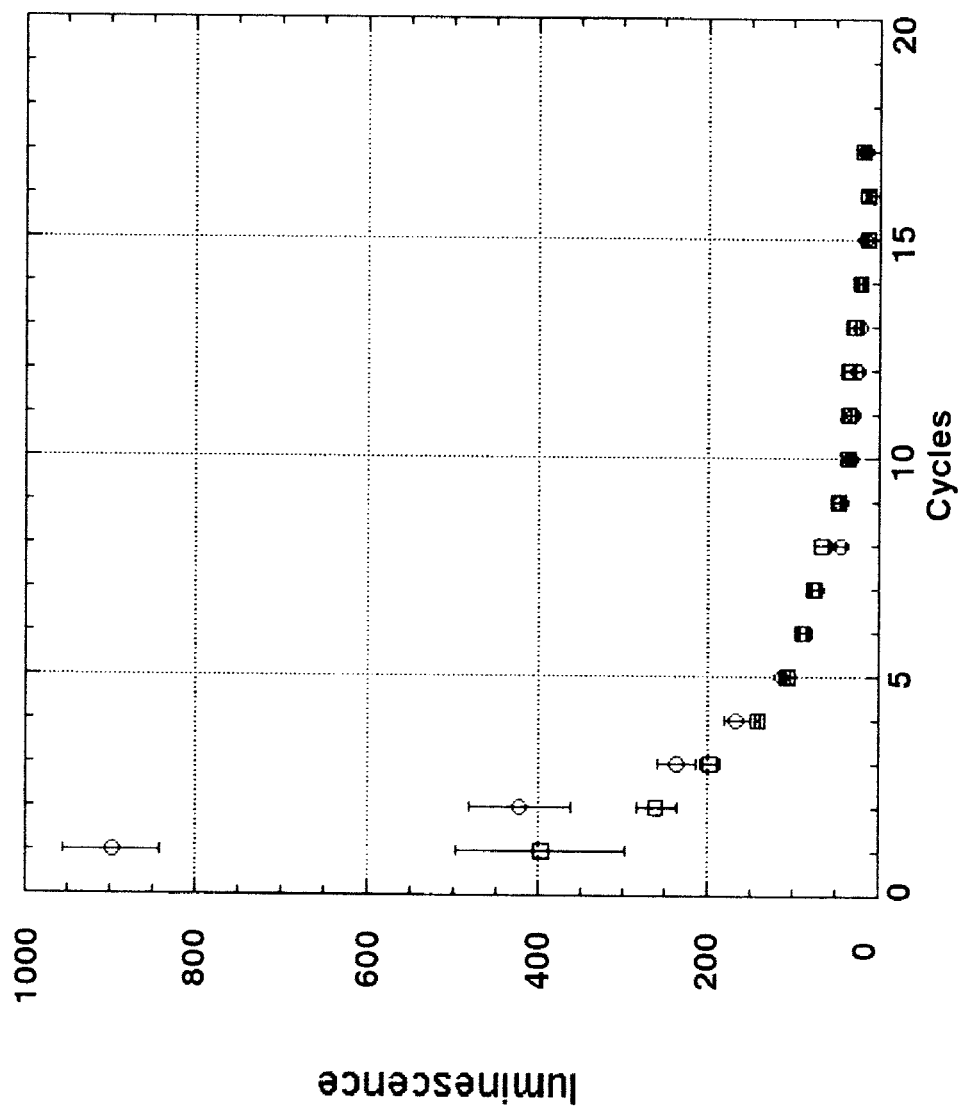
FIG. 2 shows bacteria emitted luminescence in co-cultures with wildtype or transgenic yeast FIG. 3 graphically illustrates the area under the curves in FIG. 2. The area under the curve is statistically significant by T-test ($p<0.05$) for the first few cycles.
Figure 3:
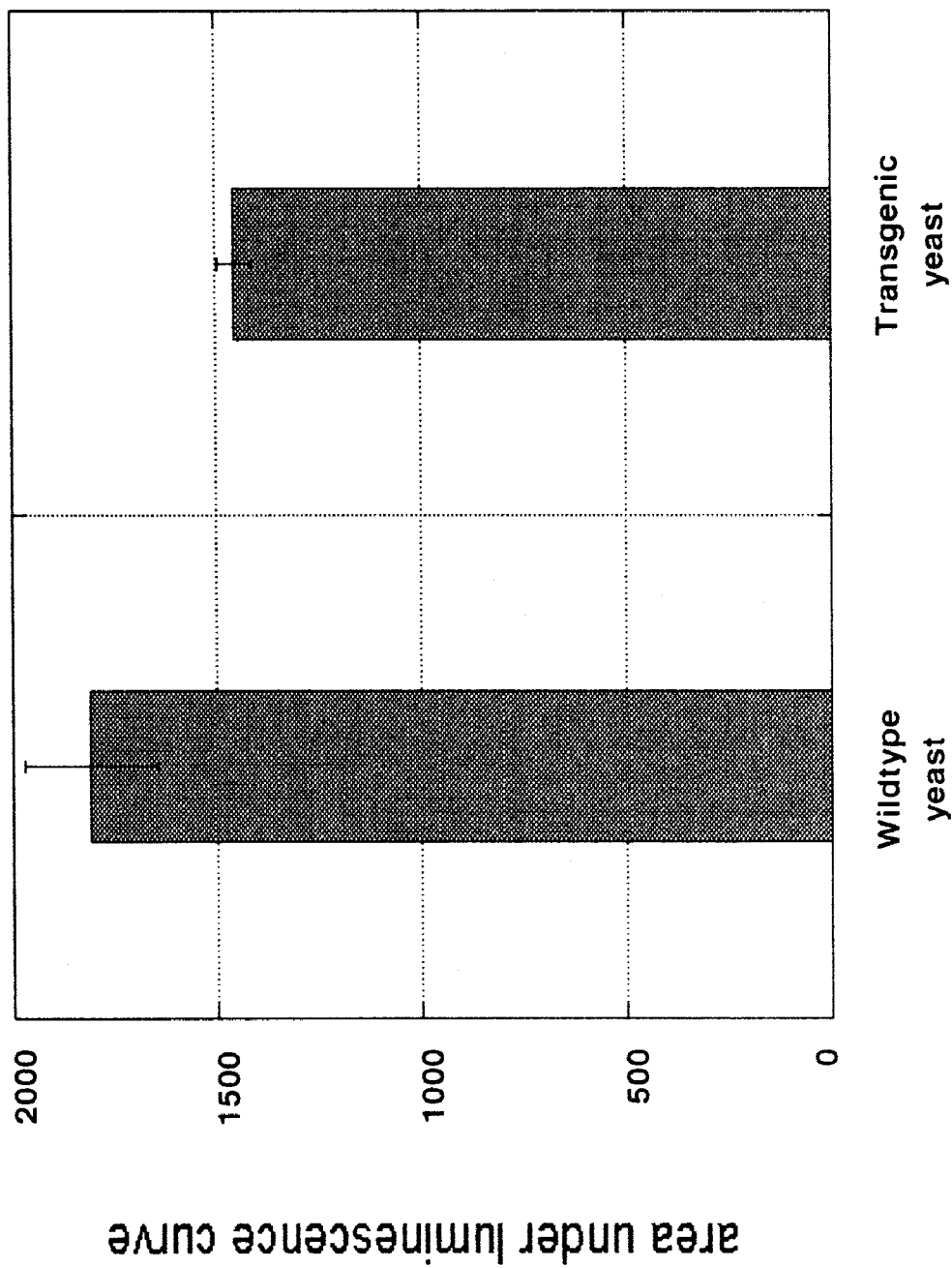
Figure 4:
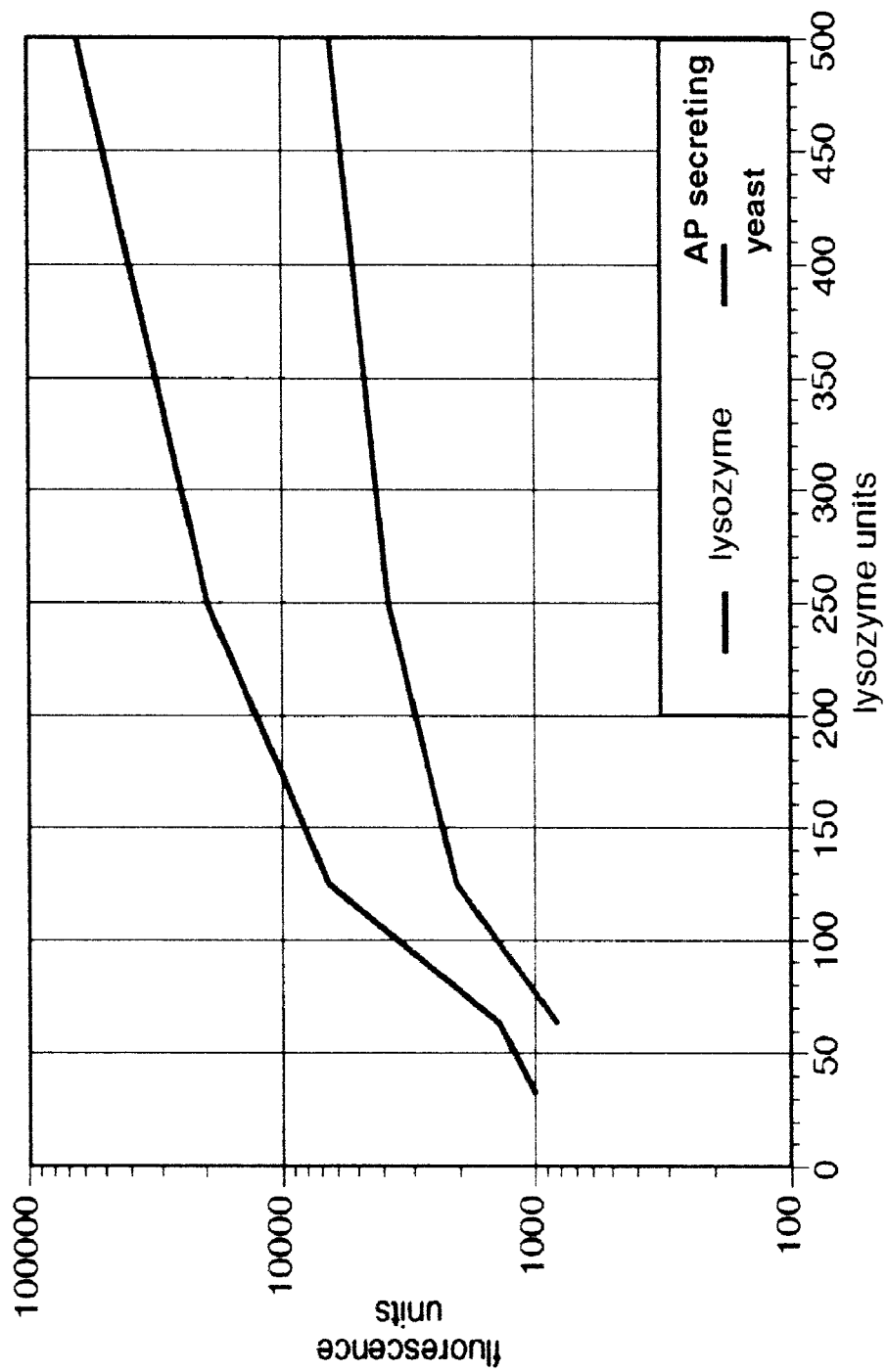
FIG. 4 graphical illustration of antibacterial activity in AP secreting yeast.

To determine if the cloned yeast expressed the inserted AP, supernatants were extracted from three separate yeast colonies. The supernatants were analyzed by Liquid chromatography-mass spectrometry (LC-MS) analysis. The LC/MS chromatograms of three yeast cell supernatants showed that the yeast were expressing the nisin transgene product (FIGS. 2, 3, and 4). The MS peak at 701 indicates the presence of the expressed nisin transgene in the supernatant. The 697 peak is a non-transgenic natural product of the yeast. Further, the small peaks close to 701 are the radioisotope variants that are commonly observed.

Example 4

Antibacterial Activity in AP Secreting Yeast

Antibacterial activity in yeast culture supernatants was tested against 3 target strains of lactic acid bacteria including *Enterococcu faecalis* 32, *Lactobacillus acidophilus* (ATCC), and *Pediococcus pentosaceus*. The method was a modification of the protocol described in Berjeaud et al. Appl Microbiol. Biotechol. 57:757-763, 2001. Each species was transformed with pLSYC02, a plasmid carrying the luxA::B fusion proteins controlled by the lactococcal p59 promoter and an erythromycin resistance gene. The luxA:B fusion protein causes luminescent light emission when living bacteria are exposed to nonaldehyde. Killed bacteria do not emit light. Bacteria were grown in phosphate buffered (pH 7) Terrific Broth with glycerol containing 150 µg/mL erythromycin (TBG). Single colonies from agar plates were used to seed overnight cultures, which were incubated at 37° C. with shaking. The next day, the cultures were diluted 1:5 in TBG, grown for one hour and then placed on ice. For the antibacterial activity assay, cells were washed in saline and aliquoted $3 \times 10^7$ per well in 50 µL of phosphate buffered saline pH 7 into 96 well opaque plates. Next, 50 µL of test supernatant or diluted authentic nisin peptide was added to each well in triplicate. Luminescence was measured in a BMG Lumistar Optima luminometer after three baseline measurements, 1 second integration at a gain of 4000, and injection of 2 µL/well of the bacterial luciferase substrate nonaldeyde. Twenty subsequent measurements were made and luminescence was compared for all wells at the cycle showing peak signal, usually cycle 10 after injection. For negative controls, K. lactis supernatants from cells bearing an integrated copy of the empty pKLAC1 expression cassette or expressing the maltose binding protein from the pKLAC1-malE expression cassette (New England Biolabs) were used. For positive controls, nisin reagent (MP Biologicals), or nisin peptide synthesized by Genscript, was used. As shown in FIG. 12, synthetic nisin that had not been modified exhibited antibacterial activity. Contrary to what is known in the art, nisin does not need to be modified to elicit antibacterial activity.

To evaluate transgenic yeast strains expressing the glucosamidase derived antibacterial protein, transgenic yeast were co-cultured with pLSYC02 transformed *Pediococcus pentosaceus* bacteria. Again, pLSYC02 carrying bacteria emit luminescent light while alive when exposed to nonaldehyde, but killed bacteria do not emit light. Transgenic and wild type *K. lactis* yeast clones were grown in 10% yeast extract, 20% bacto peptone, 2% galactose (YPG) for 36 hours at 30° C. with shaking. Galactose was used as the carbon substrate to activate the transgenic galactosidase promoter which drives expression of the transgene. Transgenic *Pediococcus pentosaceus* bacteria carrying the pLSYC02 plasmid were grown overnight in terrific broth with 1% glycerol and 10 µg/mL erythromycin (TBGE) at 37° C. with shaking. Yeast and bacteria were pelleted and resuspended in YPG. Twenty million bacterial cells and two million yeast cells were dispensed into flat bottom, opaque microtiter plates in 100 µL aliquots (final total volume). After 3 cycles of measuring background luminescence, 5 µL nonyl aldehyde (Acros Organics, 95%) was injected into each well except for blank wells, and luminescence was measured for 20 cycles with shaking between each cycle in a 37° C. thermostatted BMG Lumistar Optima luminometer.

Yeast strains expressing the glucosamidase derived antibacterial protein showed antibacterial activity when co-cultured with *Pediococcus pentosaceus* bacteria (FIGS. 2 and 3). Over the course of about 3 cycles, luminescence detection significantly decreased indicating a decrease in live bacteria. In the co-culture containing the glucosamidase derived antibacterial protein expressing yeast compared to the culture containing wildtype yeast. These results indicate the antibacterial protein effectively killed bacteria.

Example 5

Antibacterial Activity in AP Secreting Yeast

Antibacterial activity in yeast culture supernatants was tested against lysozymes of known enzyme activity found in hen egg whites. The test is designed to determine the activity of the bacteriophage lysine enzyme discussed in the present application. The methodology for the assay was based on the EnzChek Lysozyme Assay Kit (e-22013) produced by Invitrogen. The assay uses *Micrococcus* cell walls over-labeled with fluorescein isothiocyanate. The excess fluorescein label causes diminished fluorescence signal because of fluorophore proximity. When lysozyme activity causes molecular units to detach from the cell wall, the units carry fluorescein molecules with them, which lessens fluorophore proximity and increases overall fluorescence.

The assay was performed in 96 well plates, with each condition tested in duplicate. Test supernatants were samples of AP secreting recombinant yeast culture that have been centrifuged at 16,000×g for 5 minutes to completely remove cells and debris. The Lysozyme standard used as a control or comparative was hen egg white lysozyme dissolved in phosphate buffered saline pH 7 (PBS) at 1,000 units/ml. A two-fold dilution series was carried out six times with lysozyme standard or test supernatant as follows: 25 µL of PBS was added to all wells. In the first column of wells, 25 µL of lysozyme standard or test supernatant was added. After mixing, 25 µL were transferred to the next well. This set was repeated five more times to result in six, two-fold dilutions. 25 µL were removed from the last well and discarded. Then 25 µL of FITC-labeled *Micrococcus* cell walls (substrate), at 100 µg/ml was added to all wells. A final set of 2 wells contains 25 µL PBS and 25 µL substrate to serve as a no enzyme control. The plate was incubate at 37 C for 30 minutes, and then the fluorescence was read on a Fluodia plate reader (Photon Technologies Inc) using FITC filters and attenuation settings of ¼, ⅙ and ⅛. After subtracting the fluorescence of the no enzyme control from each well, the corrected fluorescence values were recorded and expected to reflect the maximum reaction velocity (Vmax) achieved under the assay conditions. Data was plotted as Vmax as a function of lysozyme standard activity units.

As shown in FIG. 4 the AP secreting yeast display activity similar to the lysozyme. The results demonstrate that the AP secreting yeast will cause breakdown of the cellular walls, and can be correlated with the potential breakdown of bacterial cell walls.

Example 6

Ethanol Inducible System

Methods to control lactic acid bacterial growth during fermentation include using inducible promoter systems. One such system that may be employed is the alcohol dehydrogenase I promoter system derived from *Aspergillus nidulans*.

The alcohol dehydrogenase I promoter system consists of two DNA sequence components. The first component consists of the following DNA sequences, fused together, in five prime to three prime order: 1) the alcohol dehydrogenase I promoter of *Aspergillus nidulans* (derived from Genbank M16916.1) containing the alcA binding site for the alcR transcription factor, 2) a yeast signal peptide sequence to mediate secretion of the gene product; 3) the open reading frame of the gene for any of the bacteriophage peptidoglycan-digesting catalytic domains including, but not limited to, SEQ ID NO: 1-5; and 4) a cell wall-associated protein domain specific to bacteria of the order Lactobacillaceae derived from the cell wall lytic enzyme genes of phages that infect lactic acid bacteria. The second sequence component consists of the following DNA sequences, fused together, in five prime to three prime order: 1) a constitutive promoter such as SV40; 2) an open reading frame for the alcR transcription factor protein that is derived from the gene of that function in *Aspergillus* nidulans. The two DNA sequence components may be synthesized using oligonucleotides with overlapping cohesive ends. The two DNA sequence components may be codon harmonized according to the codon usage frequency for the desired host to optimize expression properties.

In this system, the transcription factor transgene, alcR, will be constitutively expressed. When ethanol is present in the environment, the alcR transcription factor will activate transcription of the transgenic enzyme and the transgenic host cells will synthesize and secrete the lytic enzymes that are targeted to competitive bacteria in the environment.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the claims.

What is claimed is:

1. An isolated nucleic acid sequence encoding an antibacterial protein, the isolated nucleic acid sequence comprising SEQ ID NO: 5.

2. An isolated amino acid sequence comprising an antibacterial protein, the isolated amino acid sequence comprising SEQ ID NO: 10.

3. A population of cells, wherein at least one cell expresses at least one antibacterial protein that is encoded by a nucleic acid sequence comprising SEQ ID NO: 5.

4. The population of cells of claim 3, wherein the population of cells are yeast.

5. The population of cells of claim 4, wherein the yeast is selected from the group consisting of *Kluyveromyces lactis, Saccharomyces cerevisiae, Schizosaccharomyces pombe*, and *Candida albicans*.

6. A population of cells, wherein at least one cell expresses at least one antibacterial protein having an amino acid sequence comprising SEQ ID NO: 10.

7. The population of cells of claim 6, wherein the population of cells are yeast.

8. The population of cells of claim 7, wherein the yeast is selected from the group consisting of *Kluyveromyces lactis, Saccharomyces cerevisiae, Schizosaccharomyces pombe*, and *Candida albicans*.

9. An isolated microscopic transgenic organism, wherein the isolated microscopic organism expresses at least one antibacterial protein that is encoded by a nucleic acid sequence comprising SEQ ID NO: 5.

10. The transgenic organism of claim 9, wherein the antibacterial protein is expressed in response to lactic acid.

11. The transgenic organism of claim 9, wherein the antibacterial protein is expressed in response to ethanol.

12. The transgenic organism of claim 9, wherein the isolated transgenic organism is a yeast strain.

13. The transgenic organism of claim 12, wherein the yeast strain is selected from the group consisting of *Kluyveromyces lactis, Saccharomyces cerevisiae, Schizosaccharomyces pombe*, and *Candida albicans*.

14. An isolated bactericidal yeast, wherein the yeast expresses at least one antibacterial protein that is encoded by a nucleic acid sequence comprising SEQ ID NO: 5.

15. The isolated bactericidal yeast of claim 14, wherein the yeast is selected from the group consisting of *Kluyveromyces lactis, Saccharomyces cerevisiae, Schizosaccharomyces pombe*, and *Candida albicans*.

16. The isolated bactericidal yeast of claim 14, wherein the antibacterial protein is expressed in response to lactic acid.

17. The isolated bactericidal yeast of claim 14, wherein the antibacterial protein is expressed in response to ethanol.

18. An isolated bactericidal yeast, wherein the yeast expresses at least one antibacterial protein having an amino acid sequence comprising SEQ ID NO: 10.

19. The isolated bactericidal yeast of claim 18, wherein the yeast is selected from the group consisting of *Kluyveromyces lactis, Saccharomyces cerevisiae, Schizosaccharomyces pombe*, and *Candida albicans*.

20. The isolated bactericidal yeast of claim 18, wherein the antibacterial protein is expressed in response to lactic acid.

21. The isolated bactericidal yeast of claim 18, wherein the antibacterial protein is expressed in response to ethanol.

* * * * *

SEQUENCE LISTING

```
<160> NUMBER OF SEQ ID NOS: 10

<210> SEQ ID NO 1
<211> LENGTH: 911
<212> TYPE: DNA
<213> ORGANISM: Artificial
<220> FEATURE:
<223> OTHER INFORMATION: Alanine Amidase Genescript

<400> SEQUENCE: 1
ctcgagaaaa gaatgattat gttggttgca ggtcatggtt acaatgatcc aggtgctgtt      60
ggtaatggta caaatgaaag agactttatc agaaaataca taacaccaaa cattgctaag     120
tatttgagac acgccggtca tgaagttgct ctatatggtg gttcatcaca atctcaggat     180
atgtaccaag atactgctta cggtgtcaac gtaggaaaca acaaagatta tggtttgtac     240
tgggttaaat ctcatggtta cgatatagtt cttgaaatcc atcttgacgc agctggtgaa     300
tctgccagtg gtggtcatgt aattatttcc tcacaattta acgctgatac tatcgataaa     360
tctatccaag atgtcattaa gaataactta ggtcaaatta gaggtgttac ccctagaaat     420
gatttgctaa acgttaatgt tccgctgaga ttaatattaa ctatagatta tcagaactag     480
gttttattac taataagaat gacatggatt ggataaagaa aaactatgat ttgtattcaa     540
agttgattgc tggtgctatt catggtggtg gtggtggttc cggaggtggt ggatctggtg     600
gtggaggttc ttatatagtg aaacaaggtg atactttaag tggtattgct tcaaattggg     660
gtaccaattg gcaagaacta gctagacaaa atagtctttc taatccaaat atgatctata     720
caggtcaagt gatcagattc acaggtggtc agtctggtgc taccgctaga acctacacag     780
tttcatcagg tgataatttg tcctcaatag catccagatt gggtacaaca gttcaatctt     840
tggtatccat gaatggtatc tccaacccaa acttaattta tgccggacaa acccttaact     900
attaaagatc t                                                          911

<210> SEQ ID NO 2
<211> LENGTH: 1047
<212> TYPE: DNA
<213> ORGANISM: Artificial
<220> FEATURE:
<223> OTHER INFORMATION: Glucosaminidase Genescript

<400> SEQUENCE: 2
ctcgagaaaa gaatgcaagg taaggccttc gctgaagctt gtaagaagaa taatatcaat      60
gaaatttatt taattgctca cgccttttg gaatcaggtt acggtacttc taatttcgca     120
tctggtagat acggtgggta taactatttc ggtatcggtg catttgataa caatccaaac     180
tacgctatga ctttcgctaa gaataagggt tggacatctc ctgctaaagc tattatggga     240
```

```
ggtgcttcat ttgttagaaa agattatatt aatagggtca aaacactttg tatagaatca     300
gatggaaccc aaagaaccca gctacacacc aatatgctac tgcaattgaa tggtgtcaac     360
atcaagctag tactatagct aagctttata agggtggtgg aggttctggt ggtggtggaa     420
gtggtggtgg tggttcctac atcgttaaac aaggtgatac tttgtctggt attgcttcaa     480
actggggtac aaattggcaa gaattggcta gacaaaatag tttatctaat ccaaacatga     540
tttacactgg tcaagttatc agatttactg gaggtcaatc tggtcccact gccagaactt     600
atactgtttc atccggtcat aatttgtctt ctattgctag tagattggga caactgtgca     660
atctcttgtt tctatgaatg gtattagtaa tccaaactta atttacgccg gtcaaacatt     720
aaactattga agatctgtgg aggttcttat atagtgaaac aaggtgatac tttaagtggt     780
attgcttcaa attggggtac caattggcaa gaactagcta gacaaaatag tctttctaat     840
ccaaatatga tctatacagg tcaagtgatc agattcacag gtggtcagtc tggtgctacc     900
gctagaacct acacagtttc atcaggtgat aatttgtcct caatagcatc cagattgggt     960
acaacagttc aatctttggt atccatgaat ggtatctcca acccaaactt aatttatgcc    1020
ggacaaaccc ttaactatta aagatct                                        1047

<210> SEQ ID NO 3
<211> LENGTH: 979
<212> TYPE: DNA
<213> ORGANISM: Artificial
<220> FEATURE:
<223> OTHER INFORMATION: Lysozyme Genescript

<400> SEQUENCE: 3
gatcaagcca cttacgagac tcaagtcgct tccgcaatag ctcaaggaaa aagagctcat      60
acatatattt ggtatcaagt tggaggttct caagaagttg ctaaagcagc ccttgataga     120
tatttgccaa aaattcaaac tccaaagaat agtatagtgg ctttagatta cgaatccggt     180
gctagtggag ataaacaagc taacacagat gctatcttat atggtatgag aagagttaaa     240
gctgctggtt atactccaat gtattactca gataaaccat acactcttgc caacgtcaat     300
tataaacaga ttattaaaga gtttccaaac tctctatgga ttgctgctta ccaaaactac     360
gaagttaccc cagttcctaa ttattctttc ttccccttcaa tggatggtat ctcagtattc     420
caattcacta gtacttatgt tgctggtggt ttagatggaa atgtggactt gactggtatc     480
acagacaacg ttatggtaa gcaaaaagga caagaagtta agcctgatac cgctactcct     540
gctattgaga atggtaaaga agcaaatgaa gttaaggtaa cgacgttgag gttggtatga     600
cagtaaaagt taactttggt gccaagaatt acgctacagg tgaaacaatt cctcaatggg     660
taaagggtca accacataaa ataatccaaa agaacggtga tactgttttg ctagatggta     720
ttatgtcatg gttgtcagtt catgatgttg aaaccattga tgcttcaacc tcccaaccaa     780
ctaccccagc aaagagtggt ggtggtgaa gtggtggtgg tggttctggt ggtggtggat     840
catatatcgt taagcaaggt gatactcttt caggtatcgc ttctaactgg ggtacaaatt     900
ggcaagagtt ggctagacaa aatagtttat ctaatccaaa catgatctat accggtcaag     960
tcattagatt taccggtgg                                                  979

<210> SEQ ID NO 4
<211> LENGTH: 1050
<212> TYPE: DNA
<213> ORGANISM: Artificial
<220> FEATURE:
<223> OTHER INFORMATION: Peptidase Genescript
```

<400> SEQUENCE: 4

```
actgcttacg gtcatatgtg ggatgctttc gcaacaggat tgagacaagg tcagagagtc      60
gaagctggtc agttaattgc ttacgtcggt accaacggtc aatctacagg tcctcatctt     120
catttcgagg tccatccaac tgtttggaga caaggttctc aaatcgatcc aaaaccatgg     180
ttggctaatg ctagaaaccc aggtgatcca gcacctgccc cagcaccacc aaaaggtggt     240
actttagcta ccttgactga tccttttact ggagaacttt ggtctccaaa cagataccat     300
ccaagaggtc ttggtgatcc aagatggatt gttgttcaca ctcaagaagg tggtagaact     360
gctagagatt tggctgctta tcttgctcaa aagtcttctc aagtttcata ccatgtggtt     420
gtagatgaca gagaagttct aaaagttgtt gccgaaggtg atgctccatg ggcagctgct     480
ggtgctaaca aatacgcatt ccatatctgt atggctggtt cttatgcctc ctggagtaga     540
aacaagtggt tggatgtcga taccagtgac ggtaagaatg aggatttgca attgaccaaa     600
actgctcatg tgatcgcatg gtggtgcgat aagtatggta taccaccagt ttggatcggt     660
ggtagaaata ttcctccatg gggattggat ggtgtttgtg gtcatgtcga cttaggtgca     720
tggggtggag acacacagat cctggaccaa actttcctag agacgaatt aatgagaaga     780
gtttctcaat ttttggctgg tacagaatta ccaccactac caaccccacc acctgtaaca     840
gttccaggta ccaaaccaga tcaatatggt gattggatgt tgtacagagg taatggtgga     900
ggaggttctg gtggaggagg tagtggaggt ggtggtagtt acatcgttaa acaaggtgat     960
actctttctg gtattgcatc taactggggt acaaactggc aagaattggc tagacaaaac    1020
tccttgtcta atccaaatat gatctatact                                     1050
```

<210> SEQ ID NO 5
<211> LENGTH: 600
<212> TYPE: DNA
<213> ORGANISM: Artificial
<220> FEATURE:
<223> OTHER INFORMATION: Synthetic Nisin Gene Cloned

<400> SEQUENCE: 5

```
aaactgacat cgacgatctt ccaatatcgg ttccagaaga agccttgatt ggattcattg      60
acttaaccgg ggatgaagtt ccttgttgc ctgttaataa cggaacccac actggtattc     120
tattcttaaa caccaccatc gctgaagctg ctttcgctga caaggatgat ctcgagaaaa     180
gaatgattac ttctatttct ttgtgtactc caggttgtaa aactggtgct tgatgggtt     240
gtaatatgaa aactgctact tgtcattgtt ctattcatgt ttctaaataa aggccttgaa     300
tcgagaattt atacttagat aagtatgtac ttacaggtat atttctatga gatactgatg     360
tatacatgca tgataatatt taaacggtta ttagtgccga ttgtcttgtc cgataatgac     420
gttcctatca aagcaataca cttaccacct attacatggg ccaagaaaat attttcgaac     480
ttgtttagaa tattagcaca gagtatatga tgatatccgt tagattatgc atgattcatt     540
cctacaactt tttcgtagca taaggattaa ttacttggat gccaataaaa aaaaaaaaca     600
```

<210> SEQ ID NO 6
<211> LENGTH: 303
<212> TYPE: PRT
<213> ORGANISM: Artificial
<220> FEATURE:
<223> OTHER INFORMATION: Alanine Amidase Genescript

<400> SEQUENCE: 6

Leu Glu Lys Arg Met Ile Met Leu Val Ala Gly His Gly Tyr Asn Asp

```
                 1               5              10              15
        Pro Gly Ala Val Gly Asn Gly Thr Asn Glu Arg Asp Phe Ile Arg Lys
                         20                  25                  30

Tyr Ile Thr Pro Asn Ile Ala Lys Tyr Leu Arg His Ala Gly His Glu
                     35                  40                  45

Val Ala Leu Tyr Gly Gly Ser Ser Gln Ser Gln Asp Met Tyr Gln Asp
                 50                  55                  60

Thr Ala Tyr Gly Val Asn Val Gly Asn Asn Lys Asp Tyr Gly Leu Tyr
         65                  70                  75                  80

Trp Val Lys Ser His Gly Tyr Asp Ile Val Leu Glu Ile His Leu Asp
                             85                  90                  95

Ala Ala Gly Glu Ser Ala Ser Gly Gly His Val Ile Ile Ser Ser Gln
                        100                 105                 110

Phe Asn Ala Asp Thr Ile Asp Lys Ser Ile Gln Asp Val Ile Lys Asn
                    115                 120                 125

Asn Leu Gly Gln Ile Arg Gly Val Thr Pro Arg Asn Asp Leu Leu Asn
                    130                 135                 140

Val Asn Val Ser Ala Glu Ile Asn Ile Asn Tyr Arg Leu Ser Glu Leu
        145                 150                 155                 160

Gly Phe Ile Thr Asn Lys Asn Asp Met Asp Trp Ile Lys Lys Asn Tyr
                        165                 170                 175

Asp Leu Tyr Ser Lys Leu Ile Ala Gly Ala Ile His Gly Gly Gly
                    180                 185                 190

Gly Ser Gly Gly Gly Ser Gly Gly Gly Ser Tyr Ile Val Lys
                    195                 200                 205

Gln Gly Asp Thr Leu Ser Gly Ile Ala Ser Asn Trp Gly Thr Asn Trp
                    210                 215                 220

Gln Glu Leu Ala Arg Gln Asn Ser Leu Ser Asn Pro Asn Met Ile Tyr
        225                 230                 235                 240

Thr Gly Gln Val Ile Arg Phe Thr Gly Gly Ser Gly Ala Thr Ala
                        245                 250                 255

Arg Thr Tyr Thr Val Ser Ser Gly Asp Asn Leu Ser Ser Ile Ala Ser
                        260                 265                 270

Arg Leu Gly Thr Thr Val Gln Ser Leu Val Ser Met Asn Gly Ile Ser
                    275                 280                 285

Asn Pro Asn Leu Ile Tyr Ala Gly Gln Thr Leu Asn Tyr Arg Ser
                    290                 295                 300

<210> SEQ ID NO 7
<211> LENGTH: 246
<212> TYPE: PRT
<213> ORGANISM: Artificial
<220> FEATURE:
<223> OTHER INFORMATION: Glucosaminidase Genescript

<400> SEQUENCE: 7

Leu Glu Lys Arg Met Gln Gly Lys Ala Phe Ala Glu Ala Cys Lys Lys
        1               5                  10                  15

Asn Asn Ile Asn Glu Ile Tyr Leu Ile Ala His Ala Phe Leu Glu Ser
                        20                  25                  30

Gly Tyr Gly Thr Ser Asn Phe Ala Ser Gly Arg Tyr Gly Ala Tyr Asn
                    35                  40                  45

Tyr Phe Gly Ile Gly Ala Phe Asp Asn Asn Pro Asn Tyr Ala Met Thr
         50                  55                  60

Phe Ala Lys Asn Lys Gly Trp Thr Ser Pro Ala Lys Ala Ile Met Gly
        65                  70                  75                  80
```

```
Gly Ala Ser Phe Val Arg Lys Asp Tyr Ile Asn Lys Gly Gln Asn Thr
                85                  90                  95

Leu Tyr Arg Ile Arg Trp Asn Pro Lys Asn Pro Ala Thr His Gln Tyr
            100                 105                 110

Ala Thr Ala Ile Glu Trp Cys Gln His Gln Ala Ser Thr Ile Ala Lys
        115                 120                 125

Leu Tyr Lys Gly Gly Gly Gly Ser Gly Gly Gly Ser Gly Gly Gly Gly
    130                 135                 140

Gly Ser Tyr Ile Val Lys Gln Gly Asp Thr Leu Ser Gly Ile Ala Ser
145                 150                 155                 160

Asn Trp Gly Thr Asn Trp Gln Glu Leu Ala Arg Gln Asn Ser Leu Ser
                165                 170                 175

Asn Pro Asn Met Ile Tyr Thr Gly Gln Val Ile Arg Phe Thr Gly Gly
            180                 185                 190

Gln Ser Gly Gly Ala Thr Ala Arg Thr Tyr Thr Val Ser Ser Gly Asp
        195                 200                 205

Asn Leu Ser Ser Ile Ala Ser Arg Leu Gly Thr Thr Val Gln Ser Leu
    210                 215                 220

Val Ser Met Asn Gly Ile Ser Asn Pro Asn Leu Ile Tyr Ala Gly Gln
225                 230                 235                 240

Thr Leu Asn Tyr Arg Ser
                245

<210> SEQ ID NO 8
<211> LENGTH: 450
<212> TYPE: PRT
<213> ORGANISM: Artificial
<220> FEATURE:
<223> OTHER INFORMATION: Lysozyme Genescript

<400> SEQUENCE: 8

Leu Glu Lys Arg Met Lys Leu Ile Lys Ser Ala Ile Gly Met
1               5                   10                  15

Phe Ala Phe Phe Val Val Ala Ala Ser Gly Pro Val Phe Ala Ala Val
            20                  25                  30

Gly Asp Gln Gly Val Asp Trp Ser Lys Tyr Asn Gly Thr Tyr Gly Asn
        35                  40                  45

Phe Gly Tyr Ala His Asp Lys Phe Ala Phe Ser Gln Ile Gly Gly Thr
    50                  55                  60

Tyr Gly Gly Thr Phe Val Asp Gln Ala Thr Tyr Glu Thr Gln Val Ala
65                  70                  75                  80

Ser Ala Ile Ala Gln Gly Lys Arg Ala His Thr Tyr Ile Trp Tyr Gln
                85                  90                  95

Val Gly Gly Ser Gln Glu Val Ala Lys Ala Ala Leu Asp Arg Tyr Leu
            100                 105                 110

Pro Lys Ile Gln Thr Pro Lys Asn Ser Ile Val Ala Leu Asp Tyr Glu
        115                 120                 125

Ser Gly Ala Ser Gly Asp Lys Gln Ala Asn Thr Asp Ala Ile Leu Tyr
    130                 135                 140

Gly Met Arg Arg Val Lys Ala Ala Gly Tyr Thr Pro Met Tyr Tyr Ser
145                 150                 155                 160

Asp Lys Pro Tyr Thr Leu Ala Asn Val Asn Tyr Lys Gln Ile Ile Lys
                165                 170                 175

Glu Phe Pro Asn Ser Leu Trp Ile Ala Ala Tyr Pro Asn Tyr Glu Val
            180                 185                 190
```

```
Thr Pro Val Pro Asn Tyr Ser Phe Phe Pro Ser Met Asp Gly Ile Ser
            195                 200                 205

Val Phe Gln Phe Thr Ser Thr Tyr Val Ala Gly Gly Leu Asp Gly Asn
    210                 215                 220

Val Asp Leu Thr Gly Ile Thr Asp Asn Gly Tyr Gly Lys Gln Lys Gly
225                 230                 235                 240

Gln Glu Val Lys Pro Asp Thr Ala Thr Pro Ala Ile Glu Asn Gly Lys
                245                 250                 255

Glu Ala Asn Glu Val Lys Gly Asn Asp Val Glu Val Gly Met Thr Val
            260                 265                 270

Lys Val Asn Phe Gly Ala Lys Asn Tyr Ala Thr Gly Glu Thr Ile Pro
    275                 280                 285

Gln Trp Val Lys Gly Gln Pro His Lys Ile Ile Gln Lys Asn Gly Asp
290                 295                 300

Thr Val Leu Leu Asp Gly Ile Met Ser Trp Leu Ser Val His Asp Val
305                 310                 315                 320

Glu Thr Ile Asp Ala Ser Thr Ser Gln Pro Thr Thr Pro Ala Lys Ser
                325                 330                 335

Gly Gly Gly Gly Ser Gly Gly Gly Ser Gly Gly Gly Gly Ser Tyr
            340                 345                 350

Ile Val Lys Gln Gly Asp Thr Leu Ser Gly Ile Ala Ser Asn Trp Gly
    355                 360                 365

Thr Asn Trp Gln Glu Leu Ala Arg Gln Asn Ser Leu Ser Asn Pro Asn
370                 375                 380

Met Ile Tyr Thr Gly Gln Val Ile Arg Phe Thr Gly Gly Gln Ser Gly
385                 390                 395                 400

Ala Thr Ala Arg Thr Tyr Thr Val Ser Ser Gly Asp Asn Leu Ser Ser
                405                 410                 415

Ile Ala Ser Arg Leu Gly Thr Thr Val Gln Ser Leu Val Ser Met Asn
            420                 425                 430

Gly Ile Ser Asn Pro Asn Leu Ile Tyr Ala Gly Gln Thr Leu Asn Tyr
    435                 440                 445

Arg Ser
    450

<210> SEQ ID NO 9
<211> LENGTH: 482
<212> TYPE: PRT
<213> ORGANISM: Artificial
<220> FEATURE:
<223> OTHER INFORMATION: Peptidase Genescript

<400> SEQUENCE: 9

Leu Glu Lys Arg Met Arg Ala Gly Thr Tyr Thr Leu Ser Ser Gly Phe
1               5                   10                  15

Gly Pro Arg Trp Gly Ser Gln His Arg Gly Leu Asp Phe Ala Ala Lys
            20                  25                  30

Asp Gly Thr Pro Ile Tyr Ala Ala Gln Gly Gly Thr Val Ala Tyr Ile
        35                  40                  45

Gly Arg Ala Asp Gly Phe Gly Gln Trp Ile Val Ile Asp His Pro Ala
    50                  55                  60

Ala Asp Gly Gly Thr Thr Val Tyr Gly His Met Trp Asp Ala Phe
65                  70                  75                  80

Ala Thr Gly Leu Arg Gln Gly Gln Arg Val Glu Ala Gly Gln Leu Ile
                85                  90                  95

Ala Tyr Val Gly Thr Asn Gly Gln Ser Thr Gly Pro His Leu His Phe
```

```
            100                 105                 110
Glu Val His Pro Thr Val Trp Arg Gln Gly Ser Gln Ile Asp Pro Lys
            115                 120                 125

Pro Trp Leu Ala Asn Ala Arg Asn Pro Gly Asp Pro Ala Pro Ala Pro
        130                 135                 140

Ala Pro Pro Lys Gly Gly Thr Leu Ala Thr Leu Thr Asp Pro Phe Thr
145                 150                 155                 160

Gly Glu Leu Trp Ser Pro Asn Arg Tyr His Pro Arg Gly Leu Gly Asp
                165                 170                 175

Pro Arg Trp Ile Val Val His Thr Gln Glu Gly Gly Arg Thr Ala Arg
            180                 185                 190

Asp Leu Ala Ala Tyr Leu Ala Gln Lys Ser Ser Gln Val Ser Tyr His
            195                 200                 205

Val Val Val Asp Asp Arg Glu Val Leu Lys Val Val Ala Glu Gly Asp
        210                 215                 220

Ala Pro Trp Ala Ala Gly Ala Asn Lys Tyr Ala Phe His Ile Cys
225                 230                 235                 240

Met Ala Gly Ser Tyr Ala Ser Trp Ser Arg Asn Lys Trp Leu Asp Val
                245                 250                 255

Asp Thr Ser Asp Gly Lys Asn Glu Asp Leu Gln Leu Thr Lys Thr Ala
            260                 265                 270

His Val Ile Ala Trp Trp Cys Asp Lys Tyr Gly Ile Pro Pro Val Trp
            275                 280                 285

Ile Gly Gly Arg Asn Ile Pro Pro Trp Gly Leu Asp Gly Val Cys Gly
        290                 295                 300

His Val Asp Leu Gly Ala Trp Gly Gly Gly His Thr Asp Pro Gly Pro
305                 310                 315                 320

Asn Phe Pro Arg Asp Glu Leu Met Arg Arg Val Ser Gln Phe Leu Ala
                325                 330                 335

Gly Thr Glu Leu Pro Pro Leu Pro Thr Pro Pro Val Thr Val Pro
            340                 345                 350

Gly Thr Lys Pro Asp Gln Tyr Gly Asp Trp Met Leu Tyr Arg Gly Asn
            355                 360                 365

Gly Gly Gly Gly Ser Gly Gly Gly Ser Gly Gly Gly Ser Tyr
        370                 375                 380

Ile Val Lys Gln Gly Asp Thr Leu Ser Gly Ile Ala Ser Asn Trp Gly
385                 390                 395                 400

Thr Asn Trp Gln Glu Leu Ala Arg Gln Asn Ser Leu Ser Asn Pro Asn
                405                 410                 415

Met Ile Tyr Thr Gly Gln Val Ile Arg Phe Thr Gly Gly Gln Ser Gly
            420                 425                 430

Ala Thr Ala Arg Thr Tyr Thr Val Ser Ser Gly Asp Asn Leu Ser Ser
            435                 440                 445

Ile Ala Ser Arg Leu Gly Thr Thr Val Gln Ser Leu Val Ser Met Asn
        450                 455                 460

Gly Ile Ser Asn Pro Asn Leu Ile Tyr Ala Gly Gln Thr Leu Asn Tyr
465                 470                 475                 480

Arg Ser

<210> SEQ ID NO 10
<211> LENGTH: 235
<212> TYPE: PRT
<213> ORGANISM: Artificial
<220> FEATURE:
<223> OTHER INFORMATION: Synthetic Nisin Gene Cloned
```

```
<400> SEQUENCE: 10

Asn His Arg Arg Ser Ser Asn Ile Gly Ser Arg Arg Ser Leu Asp Trp
1               5                   10                  15

Ile His Leu Asn Arg Gly Ser Phe Leu Val Ala Cys Arg Asn Pro His
                20                  25                  30

Trp Tyr Ser Ile Leu Lys His His His Arg Ser Cys Phe Arg Gln Gly
            35                  40                  45

Ser Arg Glu Lys Asn Asp Tyr Phe Tyr Phe Val Tyr Ser Arg Leu
        50                  55                  60

Asn Trp Cys Phe Asp Gly Leu Tyr Glu Asn Cys Tyr Leu Ser Leu Phe
65                  70                  75                  80

Tyr Ser Cys Phe Ile Lys Ala Leu Asn Arg Glu Phe Ile Leu Arg Val
                85                  90                  95

Cys Thr Tyr Arg Tyr Ile Ser Met Arg Tyr Cys Ile His Ala Tyr Leu
                100                 105                 110

Asn Gly Tyr Cys Arg Leu Ser Cys Ala Ile Met Thr Phe Leu Ser Lys
            115                 120                 125

Gln Tyr Thr Tyr His Leu Leu His Gly Pro Arg Lys Tyr Phe Arg Thr
    130                 135                 140

Cys Leu Glu Tyr His Arg Val Tyr Asp Asp Ile Arg Ile Met His Asp
145                 150                 155                 160

Ser Phe Leu Gln Leu Phe Arg Ser Ile Arg Ile Asn Tyr Leu Asp Ala
                165                 170                 175

Asn Lys Lys Lys His Arg Glu Asn Phe Ser Met Leu Arg Asn Asn
            180                 185                 190

Cys Ser Val Ser Lys Lys Asp Phe His Tyr Met Phe Leu Leu Lys
            195                 200                 205

Lys Glu Asn His Gly Thr Leu Asp Leu Gln Lys Phe Asn His Arg Leu
        210                 215                 220

Thr Asp Thr Val Lys Arg Thr Thr Gly Leu Leu
225                 230                 235
```